US009790519B2

(12) United States Patent
Wei et al.

(10) Patent No.: US 9,790,519 B2

(45) Date of Patent: Oct. 17, 2017

(54) MODIFIED SEROTYPE 28 ADENOVIRAL VECTORS

(71) Applicant: GenVec, Inc., Gaithersburg, MD (US)

(72) Inventors: Lisa Wei, Gaithersburg, MD (US); Douglas E. Brough, Gaithersburg, MD (US); C. Richter King, New York, NY (US)

(73) Assignee: GenVec, Inc., Gaithersburg, MD (US)

(*) Notice: Subject to any disclaimer, the term of this patent is extended or adjusted under 35 U.S.C. 154(b) by 0 days.

(21) Appl. No.: 14/403,651

(22) PCT Filed: May 28, 2013

(86) PCT No.: PCT/US2013/042824

§ 371 (c)(1),
(2) Date: Nov. 25, 2014

(87) PCT Pub. No.: WO2013/181128

PCT Pub. Date: Dec. 5, 2013

(65) Prior Publication Data

US 2015/0167018 A1 Jun. 18, 2015

Related U.S. Application Data

(60) Provisional application No. 61/652,407, filed on May 29, 2012.

(51) Int. Cl.

| | |
|---|---|
| ***C12N 15/861*** | (2006.01) |
| ***C12N 15/00*** | (2006.01) |
| ***A61K 48/00*** | (2006.01) |
| ***C12N 15/86*** | (2006.01) |

(52) U.S. Cl.

CPC .......... *C12N 15/86* (2013.01); *A61K 48/0008* (2013.01); *A61K 48/00* (2013.01); *C12N 2710/10021* (2013.01); *C12N 2710/10043* (2013.01); *C12N 2710/10322* (2013.01); *C12N 2710/10343* (2013.01); *C12N 2710/10345* (2013.01); *C12N 2710/16634* (2013.01); *C12N 2810/6018* (2013.01)

(58) Field of Classification Search

USPC .................................... 435/320.1; 424/199.1

See application file for complete search history.

(56) References Cited

U.S. PATENT DOCUMENTS

| | | | | |
|---|---|---|---|---|
| 7,749,493 B2 * | 7/2010 | Havenga | C07K 14/005 | 424/93.2 |
| 2006/0014276 A1 * | 1/2006 | Havenga | C07K 14/005 | 435/320.1 |
| 2009/0098126 A1 * | 4/2009 | Ebner | C07K 14/005 | 424/139.1 |
| 2011/0123564 A1 * | 5/2011 | Mayall | A61K 31/713 | 424/199.1 |

FOREIGN PATENT DOCUMENTS

| | | |
|---|---|---|
| WO | WO 00/03029 A2 | 1/2000 |
| WO | WO 2011/014794 A1 | 2/2011 |

OTHER PUBLICATIONS

Bruder et al., Modification of Ad5 Hexon Hypervariable Regions Circumvents Pre-Existing Ad5 Neutralizing Antibodies and Induces Protective Immune Responses PLoS ONE Apr. 2012 | vol. 7 | Issue 4 | e33920 pp. 1-13.*

Applicants' remarks to U.S. Appl. No. 14/403,651 comprising Applicants' Attachments A and B filed on Jan. 9, 2017 pp. 1-9.*

Bruder et al., "Modification of Ad5 Hexon Hypervariable Regions Circumvents Pre-Existing Ad5 Neutralizing Antibodies and Induces Protective Immune Responses," *PLoS ONE*, 7(4): e33920 (2012).

Cartier et al., "Hematopoietic Stem Cell Gene Therapy with Lentiviral Vector in X-Linked Adrenoleukodystrophy," *Science*, 326: 818-823 (2009).

Cavazzana-Calvo et al., "Gene Therapy of Human Severe Combined Immunodeficiency (SCID)-X1 Disease," *Science*, 288 (5466): 669-672 (2000).

Chroboczek et al., "The Sequence of the Genome of Adenovirus Type 5 and Its Comparison with the Genome of Adenovirus Type 2," *Virology*, 186: 280-85 (1992).

Crawford-Miksza et al., "Analysis of 15 Adenovirus Hexon Proteins Reveals the Location and Structure of Seven Hypervariable Regions Containing Serotype-Specific Residues," *J. Virol.*, 70(3): 1836-1844 (1996).

Devaux et al., "Structure of Adenovirus Fibre. I. Analysis of Crystals of Fiber from Adenovirus Serotypes 2 and 5 by Electron Microscopy and X-ray Crystallography," *J. Molec. Biol.*, 215: 567-88 (1990).

Gall et al., "Construction and Characterization of Hexon-Chimeric Adenoviruses: Specification of Adenovirus Serotype," *J. Virol.*, 72: 10260-264 (1998).

GENBANK Accession No. AB330126.1 (dated Jun. 14, 2008).

GENBANK Accession No. AB361404.1 (dated Jul. 26, 2016).

GENBANK Accession No. AB361421.1 (dated Jul. 26, 2016).

GENBANK Accession No. ABA00010.1 (dated Oct. 4, 2005).

GENBANK Accession No. ACQ91171 (dated Aug. 13, 2010).

GENBANK Accession No. BAG48822 (dated Jun. 14, 2008).

GENBANK Accession No. BAG71098.1 (dated Jul. 26, 2016).

GENBANK Accession No. CAH18767.1 (dated Jul. 26, 2016).

GENBANK Accession No. CAR66130.1 (dated Jul. 24, 2016).

GENBANK Accession No. DQ149626.1 (dated Oct. 4, 2005).

GENBANK Accession No. FJ824826.1 (dated Aug. 13, 2010).

GENBANK Accession No. FM210554.1 (dated Jul. 24, 2016).

GENBANK Accession No. Y14242.1 (dated Apr. 18, 2005).

Gerna et al., "Grouping of Human Adenoviruses by Early Antigen Reactivity," *J. Infectious Diseases*, 145(5): 678-682 (1982).

Goins et al., "Herpes simplex virus vector-mediated gene delivery for the treatment of lower urinary tract pain," *Gene Ther.*, 16(4): 558-569 (2009).

(Continued)

*Primary Examiner* — Maria Leavitt

(74) *Attorney, Agent, or Firm* — Leydig, Voit & Mayer, Ltd.

(57) ABSTRACT

The invention provides a replication-deficient serotype 28 adenoviral vector characterized by comprising a portion of a serotype 45 adenoviral hexon protein and/or a portion of a serotype 45 fiber protein in place of the endogenous serotype 28 hexon and/or fiber protein.

13 Claims, 2 Drawing Sheets

(56) References Cited

OTHER PUBLICATIONS

Figure 1:
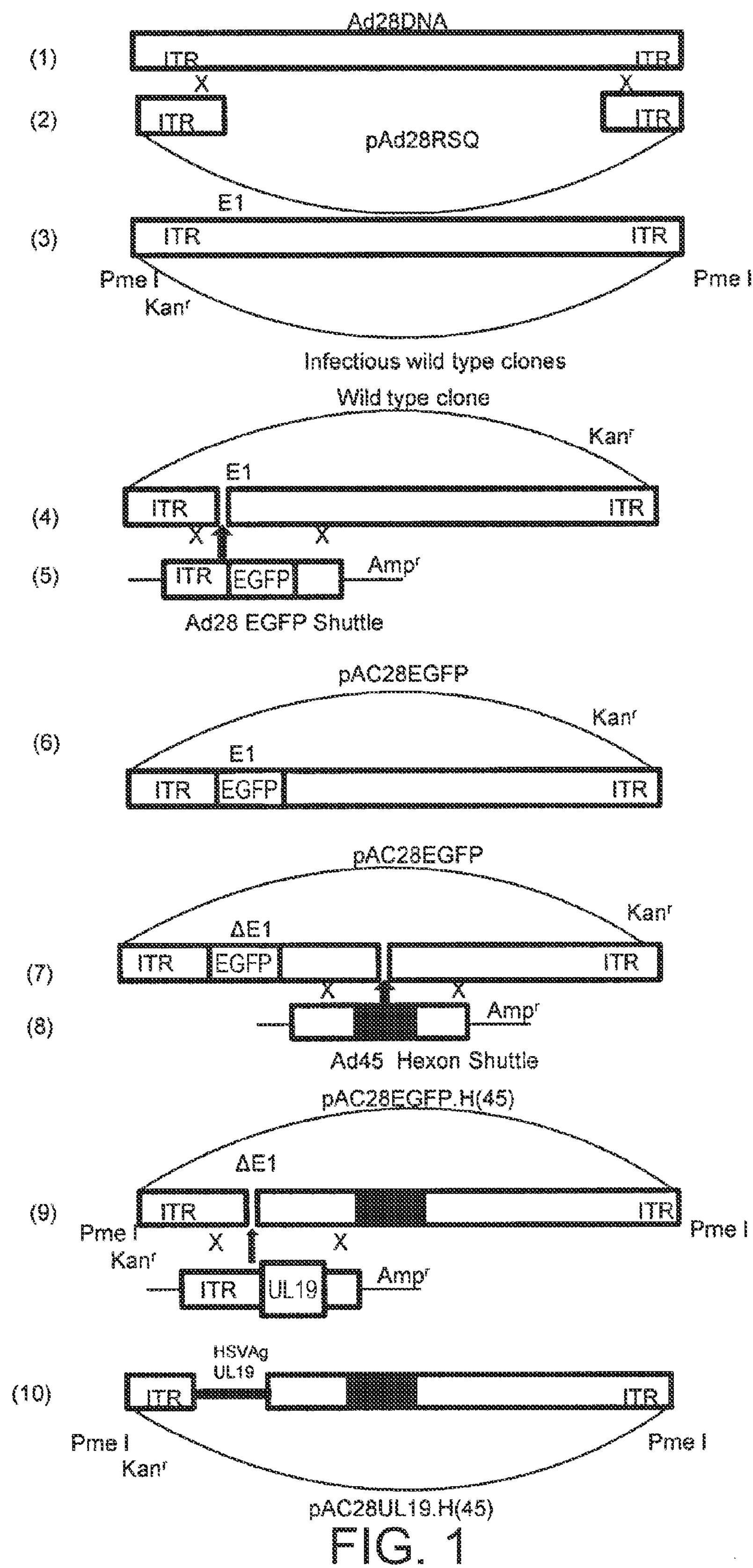

Green et al., "Evidence for a repeating cross-1β sheet structure in the adenovirus fibre," *EMBO J.*, 2: 1357-65 (1983).

Hacein-Bey-Abina et al., "A Serious Adverse Event after Successful Gene Therapy for X-Linked Severe Combined Immunodeficiency," *N. Engl. J. Med.*, 348: 255-256 (2003).

Henry et al., "Characterization of the Knob Domain of the Adenovirus Type 5 Fiber Protein Expressed in *Escherichia coli,"* *J. Virol.*, 68(8): 5239-46 (1994).

Horvath et al., "Nonpermissivity of Human Peripheral Blood Lymphocytes to Adenovirus Type 2 Infection," *J. Virology*, 62(1): 341-345 (1988).

Jornvall et al., "The Adenovirus Hexon Protein. The Primary Structure of the Polypeptide and its Correlation with the Hexon Gene," *J. Biol. Chem.*, 256(12): 6181-6186 (1981).

Kay et al., "Viral vectors for gene therapy: the art of turning infectious agents into vehicles of therapeutics," *Nature Medicine*, 7(1): 33-40 (2001).

Lasaro et al., "New Insights on Adenovirus as Vaccine Vectors," *Molecular Therapy*, 17(8): 1333-1339 (2009).

Mayrhofer et al., "Nonreplicating Vaccinia Virus Vectors Expressing the H5 Influenza Virus Hemagglutinin Produced in Modified Vero Cells Induce Robust Protection," *J. Virol.*, 83(10): 5192-5203 (2009).

Mease et al., "Safety, Tolerability, and Clinical Outcomes after Intraarticular Injection of a Recombinant Adeno-associated Vector Containing a Tumor Necrosis Factor Antagonist Gene: Results of Phase 1/2 Study," *Journal of Rheumatology*, 37(4): 692-703 (2010).

Robinson et al., "Computational analysis and identification of an emergent human adenovirus pathogen implicated in a respiratory fatality," *Virology*, 409(2): 141-147 (2011).

Rux et al., "Structural and Phylogenetic Analysis of Adenovirus Hexons by Use of High-Resolution X-Ray Crystallographic, Molecular Modeling, and Sequence-Based Methods," *J. Virol.*, 77(17): 9553-9566 (2003).

Signas et al., "Adenovirus 3 Fiber Polypeptide Gene: Implications for the Structure of the Fiber Protein," *J. Virol.*, 53: 672-78 (1985).

Silver et al., "Interaction of Human Adenovirus Serotype 2 with Human Lymphoid Cells," *Virology*, 165: 377-387 (1988).

Thomas et al., "Progress and Problems with the Use of Viral Vectors for Gene Therapy," *Nature Review Genetics*, 4: 346-358 (2003).

Yeh et al., "Human adenovirus type 41 contains two fibers," *Virus Res.*, 33: 179-98 (1991).

Rux et al., "Structural and Phylogenetic Analysis of Adenovirus Hexons by Use of High-Resolution X-Ray Crystallographic, Molecular Modeling, and Sequence-Based Methods," *Journal of Virology*, 77(17): 9553-9566 (Sep. 2003).

International Preliminary Report on Patentability for Application No. PCT/US2013/042824 (Dec. 11, 2014).

* cited by examiner

MODIFIED SEROTYPE 28 ADENOVIRAL VECTORS

CROSS-REFERENCE TO RELATED APPLICATIONS

This patent application claims the benefit of U.S. Provisional Patent Application No. 61/652,407, filed May 29, 2012, which is incorporated by reference in its entirety.

STATEMENT REGARDING FEDERALLY SPONSORED RESEARCH AND DEVELOPMENT

This invention was made with Government support under Grant Number 5R43AI077147-02 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 79,080 Byte ASCII (Text) file named "719204_ST25.TXT," created on Nov. 25, 2014.

BACKGROUND OF THE INVENTION

In vivo delivery of proteins in biologically relevant forms and amounts has been an obstacle to drug and vaccine development for decades. One solution that has proven to be a successful alternative to traditional protein delivery approaches is the use of exogenous nucleic acid sequences for production of proteins in vivo. Gene transfer vectors ideally enter a wide variety of cell types, have the capacity to accept large nucleic acid sequences, are safe, and can be produced in quantities required for treating patients. Viral vectors are gene transfer vectors with these advantageous properties (see, e.g., Thomas et al., *Nature Review Genetics,* 4: 346-358 (2003)). Furthermore, while many viral vectors are engineered to infect a broad range of cell types, viral vectors also can be modified to target specific cell types, which can enhance the therapeutic efficacy of the vector (see, e.g., Kay et al., *Nature Medicine,* 7(1): 33-40 (2001)).

Viral vectors that have been used with some success to deliver exogenous proteins to mammalian cells for therapeutic purposes include, for example, Retrovirus (see, e.g., Cavazzana-Calvo et al., *Science,* 288 (5466): 669-672 (2000)), Lentivirus (see, e.g., Cartier et al., *Science,* 326: 818-823 (2009)), Adeno-associated virus (AAV) (see, e.g., Mease et al., *Journal of Rheumatology,* 27(4): 692-703 (2010)), Herpes Simplex Virus (HSV) (see, e.g., Goins et al., *Gene Ther.,* 16(4): 558-569 (2009)), Vaccinia Virus (see, e.g., Mayrhofer et al., *J. Virol.,* 83(10): 5192-5203 (2009)), and Adenovirus (see, e.g., Lasaro and Ertl, *Molecular Therapy,* 17(8): 1333-1339 (2009)).

Despite their advantageous properties, widespread use of viral gene transfer vectors is hindered by several factors. In this respect, certain cells are not readily amenable to gene delivery by currently available viral vectors. For example, lymphocytes are impaired in the uptake of adenoviruses (Silver et al., *Virology,* 165: 377-387 (1988), and Horvath et al., *J. Virology,* 62(1): 341-345 (1988)). In addition, viral vectors that integrate into the host cell's genome (e.g., retroviral vectors) have the potential to cause insertion mutations in oncogenes (see, e.g., Cavazzana-Calvo et al., supra, and Hacein-Bey-Abina et al., *N. Engl. J. Med.,* 348: 255-256 (2003)).

The use of viral vectors for gene transfer also is impeded by the immunogenicity of viral vectors. A majority of the U.S. population has been exposed to wild-type forms of many of the viruses currently under development as gene transfer vectors (e.g., adenovirus). As a result, much of the U.S. population has developed pre-existing immunity to certain virus-based gene transfer vectors. Such vectors are quickly cleared from the bloodstream, thereby reducing the effectiveness of the vector in delivering biologically relevant amounts of a gene product. Moreover, the immunogenicity of certain viral vectors prevents efficient repeat dosing, which can be advantageous for "boosting" the immune system against pathogens when viral vectors are used in vaccine applications, thereby resulting in only a small fraction of a dose of the viral vector delivering its payload to host cells.

Thus, there remains a need for improved viral vectors that can be used to efficiently deliver genes to mammalian cells in vivo. The invention provides such viral vectors.

BRIEF SUMMARY OF THE INVENTION

The invention provides a replication-deficient serotype 28 adenoviral vector comprising one or both of the following: (a) at least a portion of an adenovirus serotype 45 hexon protein in place of at least a portion of the endogenous serotype 28 hexon protein, and (b) at least a portion of an adenovirus serotype 45 fiber protein in place of at least a portion of the endogenous serotype 28 fiber protein.

BRIEF DESCRIPTION OF THE SEVERAL VIEWS OF THE DRAWING(S)

FIG. 1 is a flow diagram of the construction of plasmid pAC28UL19.H (45) by homologous recombination. Steps 1 through 10 illustrate the homologous recombination between the Ad28 viral vector genome plasmid and the shuttle plasmid containing the Ad45 hexon followed by subsequent recombination containing the CMVTetO.UL19 expression cassette as described in Example 1.

Figure 2:
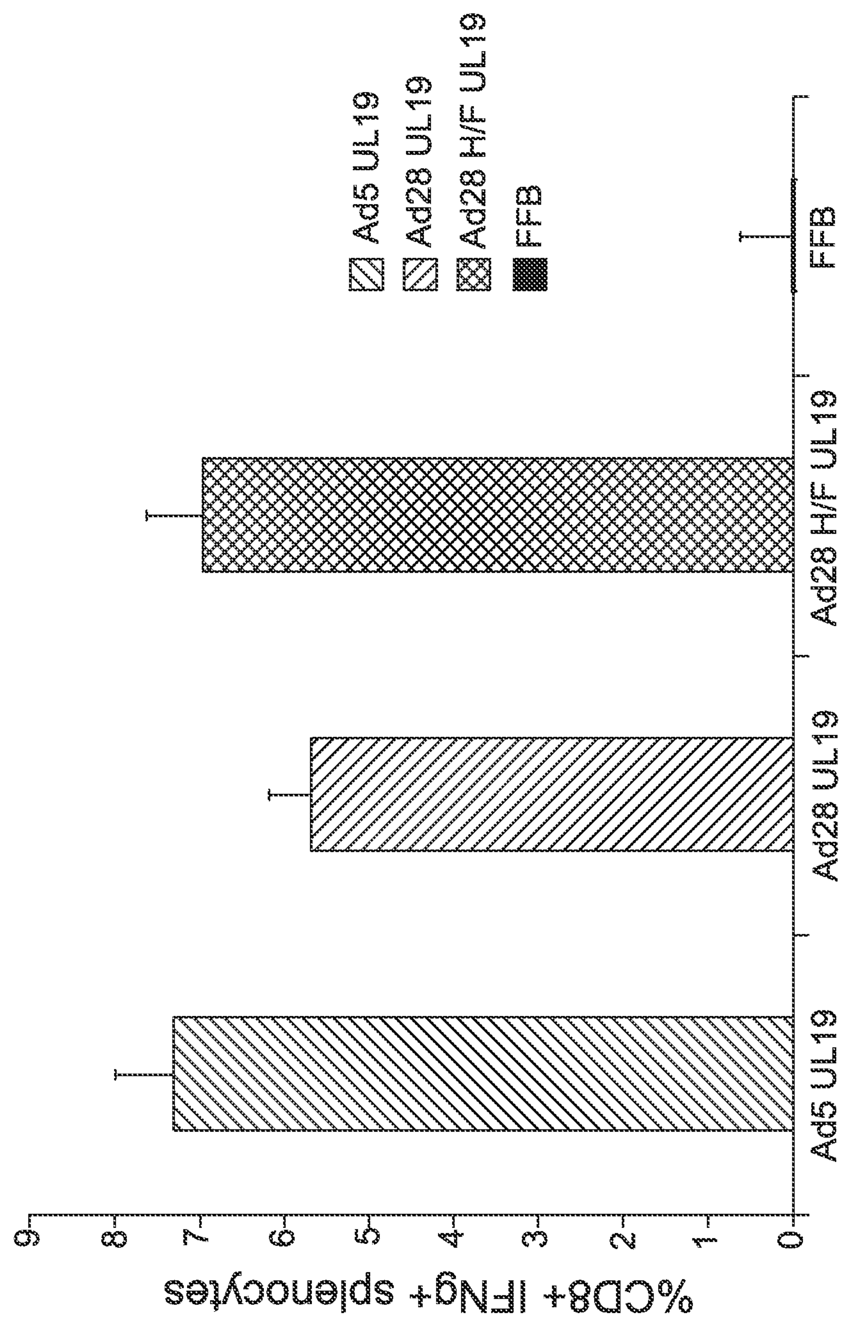

FIG. 2 is a graph depicting experimental data of CD8+ T-cell responses induced by serotype 5 and 28 adenoviral vectors encoding an HSV2 UL19 protein (Ad5 UL19 and Ad28 UL19, respectively), as well as the mutant serotype 28 adenoviral vector encoding an HSV2 UL19 protein (Ad28 H/F UL19) described in Example 2.

DETAILED DESCRIPTION OF THE INVENTION

The invention is predicated, at least in part, on the generation of an adenoviral vector based on a serotype 28 adenovirus (Ad28) containing one or more modified capsid proteins, which can effectively be used to deliver and express nucleic acid sequences encoding therapeutic proteins. It is believed that a vector based on Ad28 will provide improved delivery to human cells because Ad28 seroprevalence is low in human populations. It is also believed that a serotype 28 adenoviral vector containing a modified hexon protein and/or a modified fiber protein as described herein can stimulate a more robust T-cell response than an Ad28 vector comprising wild-type hexon and fiber proteins when used in vaccine applications.

A serotype 28 adenovirus is a member of the group D adenoviruses. In addition to Ad28, the group D adenoviruses include the following serotypes: 8, 9, 10, 13, 15, 17, 19, 20, 22, 23, 24, 25, 26, 27, 29, 30, 32, 33, 36, 37, 38, 39, 42, 43, 44, 45, 46, 47, 48, 49, 51, 53, 54, and 56 (see, e.g., Gerna et al., *J. Infectious Diseases,* 145(5): 678-682 (1982), and Robinson et al., *Virology,* 409(2): 141-147 (2011)). The genome of human Ad28 has been sequenced and is available via the GenBank database (Accession No. FJ824826.1).

The term "adenoviral vector," as used herein, refers to an adenovirus in which the adenoviral genome has been manipulated to accommodate a nucleic acid sequence that is non-native with respect to the adenoviral genome. Adenovirus is a medium-sized (90-100 nm), nonenveloped icosohedral virus containing approximately 36 kb of double-stranded DNA. There are 49 human adenoviral serotypes, categorized into 6 subgenera (A through F) based on nucleic acid comparisons, fiber protein characteristics, and biological properties (Crawford-Miksza et al., *J. Virol.,* 70: 1836-1844 (1996)). The group C viruses (e.g., serotypes 2 and 5, or Ad2 and Ad5) are well characterized, and currently are employed for gene transfer studies, including human gene therapy trials (see, e.g., Rosenfeld et al., *Science,* 252: 431-434 (1991); Rosenfeld et al., *Cell,* 68: 143-155 (1992); Zabner, *Cell,* 75: 207-216 (1993); Crystal et al., *Nat. Gen.,* 8: 42-51 (1994); Yei et al., *Gene Therapy,* 1: 192-200 (1994); Chen et al., *Proc. Natl. Acad. Sci.,* 91: 3054-3057 (1994); Yang et al., *Nat. Gen.,* 7: 362-369 (1994); Zabner et al., *Nat. Gen.,* 6: 75-83 (1994)). Typically, an adenoviral vector is generated by introducing one or more mutations (e.g., deletion, insertion, or substitution) into the adenoviral genome of the adenovirus so as to accommodate the insertion of a non-native nucleic acid sequence, for example, for gene transfer, into the adenovirus.

The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). In one embodiment of the invention, one or more capsid proteins (also referred to herein as "coat" proteins) of the adenoviral vector can be manipulated to alter the binding specificity or recognition of the vector for a viral receptor on a potential host cell. Such manipulations can include deletion of regions of the fiber or penton, insertions of various native or non-native ligands into portions of the capsid proteins, and the like. Manipulation of capsid proteins can broaden the range of cells infected by the adenoviral vector or enable targeting of the adenoviral vector to a specific cell type.

The adenoviral vector of the invention can comprise a modified hexon protein. The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, the hexon protein is a primary target for modification in order to reduce neutralization of adenoviral vectors (see, e.g., Gall et al., *J. Virol.,* 72: 10260-264 (1998), and Rux et al., *J. Virol.,* 77(17): 9553-9566 (2003)). The major structural features of the hexon protein are shared by adenoviruses across serotypes, but the hexon protein differs in size and immunological properties between serotypes (Jornvall et al., *J. Biol. Chem.,* 256(12): 6181-6186 (1981)). A comparison of 15 adenovirus hexon proteins reveals that the predominant antigenic and serotype-specific regions of the hexon protein appear to be in loops 1 and 2 (i.e., LI or l1, and LII or l2, respectively), within which are seven to nine discrete hypervariable regions (HVR1 to HVR 7 or HVR9) varying in length and sequence between adenoviral serotypes (Crawford-Miksza et al., *J. Virol.,* 70(3): 1836-1844 (1996), and Bruder et al., *PLoS ONE,* 7(4): e33920 (2012)).

The hexon protein is "modified" in that it comprises a non-native amino acid sequence in addition to or in place of a wild-type hexon amino acid sequence of the serotype 28 adenoviral vector. In this respect, at least a portion of the wild-type hexon protein (e.g., the entire hexon protein) of the inventive serotype 28 adenoviral vector desirably is removed and replaced with a corresponding portion of a hexon protein from a non-group D adenovirus (e.g., a group A, B, C, E, or F adenovirus), or an adenovirus that does not normally infect humans (e.g., a simian or gorilla adenovirus). Alternatively and preferably, at least a portion of the wild-type hexon protein of the serotype 28 adenoviral vector can be removed and replaced with a corresponding portion of a hexon protein from another group D adenovirus. For example, a portion of the wild-type hexon protein of the serotype 28 adenoviral vector can be removed and replaced with a corresponding portion of a hexon protein from any group D adenovirus (such as those described herein). Preferably, the inventive serotype 28 adenoviral vector comprises at least a portion of an adenovirus serotype 45 hexon protein in place of at least a portion of the endogenous serotype 28 hexon protein. Any suitable amino acid residue(s) of a wild-type hexon protein of the serotype 28 adenoviral vector can be modified or removed, so long as viral capsid assembly is not impeded. Similarly, amino acids can be added to the hexon protein as long as the structural integrity of the capsid is maintained. In a preferred embodiment, at least 50% (e.g., at least 55%, at least 60%, at least 65%, at least 70%, at least 75%, at least 80%, at least 85%, at least 90%, at least 95%, or 100%) of the endogenous Ad28 hexon protein is modified or removed.

A "portion" of an amino acid sequence comprises at least three amino acids (e.g., about 3 to about 800 amino acids). Preferably, a "portion" comprises 10 or more (e.g., 10 or more, 15 or more, 20 or more, 25 or more, 30 or more, 40 or more, 50 or more, or 100 or more) amino acid residues, but less than the entire wild-type hexon protein (e.g., 900 or less, 800 or less, 700 or less, 600 or less, 500 or less, 400 or less, 300 or less, 200 or less, or 100 or less amino acid residues). For example, a portion can be about 10 to about 700 amino acids (e.g., about 10, 100, 300, 500, or 600 amino acids), about 10 to about 500 amino acids (e.g., about 20, 50, 200, or 400 amino acids), or about 10 to about 300 amino acids (e.g., about 15, 40, 60, 70, 90, 150, 250, or 290 amino acids), or a range defined by any two of the foregoing values. More preferably, a "portion" comprises no more than about 600 amino acids (e.g., about 10 to about 550 amino acids, about 10 to about 500 amino acids, or about 50 to about 300 amino acids, or a range defined by any two of the foregoing values).

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

Desirably, the portion of an adenovirus serotype 45 hexon protein comprises at least one hypervariable region (HVR) in place of an endogenous Ad28 HVR. Thus, at least one HVR of the hexon protein of the inventive serotype 28 adenoviral vector is removed and replaced with at least one HVR from a wild-type serotype 45 adenovirus. In one embodiment, the serotype 28 adenoviral vector can comprise one or more of HVR1, HVR2, HVR3, HVR4, HVR5, HVR6, HVR7, HVR8, or HVR9 of a wild-type serotype 45 adenovirus hexon protein in place of the corresponding endogenous Ad28 HVR. Preferably, two or more (e.g., 2, 3, 4, 5, 6, 7, 8, or 9) HVRs of the hexon protein of the serotype 28 adenoviral vector are removed and replaced with corresponding HVRs from a serotype 45 adenovirus. More preferably, the inventive serotype 28 adenoviral vector comprises all nine HVRs of a serotype 45 adenovirus hexon protein in place of the corresponding endogenous Ad28 HVRs. In one embodiment, the entire wild-type hexon protein of the serotype 28 adenoviral vector is replaced with the entire hexon protein of a serotype 45 adenovirus.

Nucleic acid sequences that encode all or a portion of a serotype 28 or 45 adenovirus hexon protein are publicly available (see, e.g., GenBank Accession Nos. DQ149626.1 and AB330126.1). Amino acid sequences that comprise a full-length serotype 28 or 45 adenovirus hexon protein, or portions thereof, also are publicly available (see, e.g., GenBank Accession Nos. ABA00010.1 and BAG48822). In one embodiment, the portion of an adenovirus serotype 45 hexon protein comprises, for example, the amino acid sequence of SEQ ID NO: 1, and a nucleic acid sequence that encodes a portion of a serotype 45 adenovirus hexon protein comprises, for example, SEQ ID NO: 2. In another embodiment, the portion of an adenovirus serotype 45 hexon protein comprises an amino acid sequence that is at least 91.4% identical (e.g., at least 91.5% identical, at least 92% identical, at least 92.5% identical, at least 93% identical, at least 93.5% identical, at least 94% identical, at least 94.5% identical, at least 95% identical, at least 95.5% identical, at least 96% identical, at least 96.5% identical, at least 97% identical, at least 97.5% identical, at least 98% identical, at least 98.5% identical, at least 99% identical, or at least 99.5% identical) to SEQ ID NO: 1.

Nucleic acid or amino acid sequence "identity," as described herein, can be determined by comparing a nucleic acid or amino acid sequence of interest to a reference nucleic acid or amino acid sequence. The number of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.,* 215(3): 403-410 (1990); Beigert et al., *Proc. Natl. Acad. Sci. USA,* 106(10): 3770-3775 (2009); Durbin et al., eds., *Biological Sequence Analysis: Probalistic Models of Proteins and Nucleic Acids*, Cambridge University Press, Cambridge, U.K. (2009), Soding, *Bioinformatics,* 21(7): 951-960 (2005); Altschul et al., *Nucleic Acids Res.,* 25(17): 3389-3402 (1997); and Gusfield, *Algorithms on Strings, Trees and Sequences*, Cambridge University Press, Cambridge, U.K. (1997)).

The adenoviral vector of the invention can comprise a modified fiber protein. The adenovirus fiber protein is a homotrimer of the adenoviral polypeptide IV that has three domains: the tail, shaft, and knob (Devaux et al., *J. Molec. Biol.,* 215: 567-88 (1990), and Yeh et al., *Virus Res.,* 33: 179-98 (1991)). The fiber protein mediates primary viral binding to receptors on the cell surface via the knob and the shaft domains (Henry et al., *J. Virol.,* 68(8): 5239-46 (1994)). The amino acid sequences for trimerization are located in the knob, which appears necessary for the amino terminus of the fiber (the tail) to properly associate with the penton base (Novelli et al., *Virology,* 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.,* 2: 1357-65 (1983), Chroboczek et al., *Virology,* 186: 280-85 (1992), and Signas et al., *J. Virol.,* 53: 672-78 (1985)). Thus, the fiber protein has multiple functions that are key to the life cycle of adenovirus.

The fiber protein is "modified" in that it comprises a non-native amino acid sequence, in addition to or in place of a wild-type fiber amino acid sequence of the inventive serotype 28 adenoviral vector. In this respect, a portion of the wild-type fiber protein (e.g., the fiber tail, the fiber shaft, the fiber knob, or the entire fiber protein) of the inventive serotype 28 adenoviral vector can be removed and replaced with a corresponding portion of a fiber protein from a non-group D adenovirus (e.g., a group A, B, C, E, or F adenovirus), or an adenovirus that does not infect humans (e.g., a simian or gorilla adenovirus). Alternatively and preferably, at least a portion of the wild-type fiber protein of the inventive serotype 28 adenoviral vector can be removed and replaced with a corresponding portion of a fiber protein from another group D adenovirus. For example, a portion of the wild-type fiber protein of the inventive serotype 28 adenoviral vector can be removed and replaced with a corresponding portion of a fiber protein from any group D adenovirus (such as those described herein). Preferably, the inventive serotype 28 adenoviral vector comprises at least a portion of an adenovirus serotype 45 fiber protein in place of at least a portion of the endogenous serotype 28 fiber protein. Any suitable amino acid residue(s) of a wild-type fiber protein of the serotype 28 adenoviral vector that mediates or assists in the interaction between the fiber knob and the native cellular receptor can be modified or removed, so long as the fiber protein is able to trimerize. Similarly, amino acids can be added to the fiber knob as long as the fiber protein retains the ability to trimerize. In a preferred embodiment, at least 75% (e.g., at least 80%, at least 85%, at least 90%, at least 95%, or 100%) of the endogenous Ad28 fiber protein is modified or removed.

Nucleic acid sequences that encode all or a portion of a serotype 28 or 45 adenovirus fiber protein are publicly available (see, e.g., GenBank Accession Nos. AB361404.1, Y14242.1, FM210554.1, and AB361421.1). Amino acid sequences that comprise a full-length serotype 28 or 45 adenovirus fiber protein, or portions thereof, also are publicly available (see, e.g., GenBank Accession Nos. ACQ91171, CAR66130.1, BAG71098.1, and CAH18767.1). In one embodiment, the portion of an adenovirus serotype 45 fiber protein comprises the amino acid sequence of SEQ ID NO: 3, and a nucleic acid sequence that encodes a portion of a serotype 45 adenovirus fiber protein comprises, for example, SEQ ID NO: 4. In another embodiment, the portion of an adenovirus serotype 45 fiber protein comprises an amino acid sequence that is at least 67% identical (e.g., at least 68% identical, at least 69% identical, at least 70% identical, at least 71% identical, at least 72% identical, at least 73% identical, at least 74% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, or at least 99% identical) to SEQ ID NO: 3.

The inventive serotype 28 adenoviral vector comprises the aforementioned modified hexon protein, the aforementioned modified fiber protein, or the modified hexon protein and the modified fiber protein. For example, the inventive serotype 28 adenoviral vector comprises at least a portion of an adenovirus serotype 45 hexon protein in place of at least a portion of the endogenous serotype 28 hexon protein, or at least a portion of an adenovirus serotype 45 fiber protein in place of at least a portion of the endogenous serotype 28 fiber protein. Alternatively, the inventive serotype 28 adenoviral vector comprises at least a portion of an adenovirus serotype 45 hexon protein in place of at least a portion of the endogenous serotype 28 hexon protein, and at least a portion of an adenovirus serotype 45 fiber protein in place of at least a portion of the endogenous serotype 28 fiber protein.

Modifications to adenovirus coat proteins, including methods for generating chimeric hexon and fiber proteins, are described in, for example, e.g., U.S. Pat. Nos. 5,543,328; 5,559,099; 5,712,136; 5,731,190; 5,756,086; 5,770,442; 5,846,782; 5,871,727; 5,885,808; 5,922,315; 5,962,311; 5,965,541; 6,057,155; 6,127,525; 6,153,435; 6,329,190; 6,455,314; 6,465,253; 6,576,456; 6,649,407; and 6,740,525; U.S. Patent Application Publications 2001/0047081 A1, 2002/0099024 A1, 2002/0151027 A1, 2003/0022355 A1, and 2003/0099619 A1, and International Patent Application Publications WO 1996/007734, WO 1996/026281, WO 1997/020051, WO 1998/007865, WO 1998/007877, WO 1998/040509, WO 1998/054346, WO 2000/015823, WO 2001/058940, and WO 2001/092549.

The adenoviral vector can be replication-competent, conditionally replication-competent, or replication-deficient.

A replication-competent adenoviral vector can replicate in typical host cells, i.e., cells typically capable of being infected by an adenovirus. A replication-competent adenoviral vector can have one or more mutations as compared to the wild-type adenovirus (e.g., one or more deletions, insertions, and/or substitutions) in the adenoviral genome that do not inhibit viral replication in host cells. For example, the adenoviral vector can have a partial or entire deletion of the adenoviral early region known as the E3 region, which is not essential for propagation of the adenoviral genome.

A conditionally-replicating adenoviral vector is an adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenoviral vector is an adenoviral vector that requires complementation of one or more gene functions or regions of the adenoviral genome that are required for replication, as a result of, for example, a deficiency in the one or more replication-essential gene function or regions, such that the adenoviral vector does not replicate in typical host cells, especially those in a human to be infected by the adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenoviral vector is replication-competent or replication-deficient, the adenoviral vector retains at least a portion of a serotype 28 adenoviral genome. The adenoviral vector can comprise any portion of a serotype 28 adenoviral genome, including protein coding and non-protein coding regions. Desirably, the adenoviral vector comprises at least one nucleic acid sequence that encodes a serotype 28 adenovirus protein. The adenoviral vector can comprise any suitable adenovirus protein, or a nucleic acid sequence that encodes any suitable adenovirus protein, such as, for example, a protein of any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenoviral vector desirably comprises one or more amino acid sequences of the pIX protein, the penton protein, the p100 protein, the L1 52/55K protein of a serotype 28 adenovirus, or any combination of the foregoing. The adenoviral vector can comprise a full-length amino acid sequence of a serotype 28 adenovirus protein. Alternatively, the adenoviral vector can comprise a portion of a full-length amino acid sequence of a serotype 28 adenovirus protein. An amino acid sequence of a serotype 28 adenovirus pIX protein comprises, for example, SEQ ID NO: 5. An amino acid sequence of a serotype 28 adenovirus penton protein comprises, for example, SEQ ID NO: 6. An amino acid sequence of a serotype 28 adenovirus p100 protein comprises, for example, SEQ ID NO: 7. An amino acid sequence of a serotype 28 adenovirus L1 52/55K protein comprises, for example, SEQ ID NO: 8. The adenoviral vector also desirably comprises a nucleic acid sequence encoding a DNA polymerase protein of a serotype 28 adenovirus or a portion thereof. A nucleic acid sequence encoding a DNA polymerase of a serotype 28 adenovirus comprises, for example, SEQ ID NO: 9. The adenoviral vector desirably comprises one or more of SEQ ID NOs: 5-9.

In another embodiment, the invention provides a virus-like particle comprising one or more amino acid sequences of the pIX protein, the penton protein, the p100 protein, the L1 52/55K protein of a serotype 28 adenovirus, or any combination of the foregoing, as well as the serotype 45 hexon protein and/or the serotype 45 fiber protein described herein. A "virus-like particle" consists of one or more viral coat proteins that assemble into viral particles, but lacks any viral genetic material (see, e.g., Miyanohara et al., *J. Virol.,* 59: 176-180 (1986), Gheysen et al., *Cell,* 59: 103-112 (1989), and Buonaguro et al., *ASHI Quarterly,* 29: 78-80 (2005)).

Preferably, the adenoviral vector is replication-deficient, such that the replication-deficient adenoviral vector requires complementation of at least one replication-essential gene function of one or more regions of the adenoviral genome for propagation (e.g., to form adenoviral vector particles).

The replication-deficient adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad)). See Morsy et al., *Proc. Natl. Acad. Sci. USA,* 95: 965-976 (1998); Chen et al., *Proc. Natl. Acad. Sci. USA,* 94: 1645-1650 (1997); and Kochanek et al., *Hum. Gene Ther.,* 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The late regions of the adenoviral genome include the L1, L2, L3, L4, and L5 regions. The adenoviral vector also can have a mutation in the major late promoter (MLP), as discussed in International Patent Application Publication WO 2000/000628, which can render the adenoviral vector replication-deficient if desired.

The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the deficiency in the E1A subregion and/or the E1B subregion of the adenoviral genome for the adenoviral vector to propagate (e.g., to form adenoviral vector particles).

The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the deficiency in the E2A subregion and/or the E2B subregion of the adenoviral genome for the adenoviral vector to propagate (e.g., to form adenoviral vector particles).

The E3 region does not include any replication-essential gene functions, such that a deletion of the E3 region in part or in whole does not require complementation of any gene functions in the E3 region for the adenoviral vector to propagate (e.g., to form adenoviral vector particles). In the context of the invention, the E3 region is defined as the region that initiates with the open reading frame that encodes a protein with high homology to the 12.5K protein from the E3 region of human adenovirus 28 (NCBI reference sequence FJ824826) and ends with the open reading frame that encodes a protein with high homology to the 14.7K protein from the E3 region of human adenovirus 28 (NCBI reference sequence FJ824826). The E3 region may be deleted in whole or in part, or retained in whole or in part. The size of the deletion may be tailored so as to retain an adenoviral vector whose genome closely matches the optimum genome packaging size. A larger deletion will accommodate the insertion of larger heterologous nucleic acid sequences in the adenoviral genome. In one embodiment of the invention, the L4 polyadenylation signal sequences, which reside in the E3 region, are retained.

The E4 region comprises multiple open reading frames (ORFs). An adenoviral vector with a deletion of all of the open reading frames of the E4 region except ORF6, and in some cases ORF3, does not require complementation of any gene functions in the E4 region for the adenoviral vector to propagate (e.g., to form adenoviral vector particles). Conversely, an adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the deficiency in the E4 region (specifically, of ORF6 and/or ORF3 of the E4 region) for the adenoviral vector to propagate (e.g., to form adenoviral vector particles).

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region. In other words, the adenoviral vector requires, at most, complementation of a deficiency in one or more early regions of the adenoviral genome for propagation.

The replication-deficient adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenoviral vector can be deficient in other respects that are not replication-essential. For example, the adenoviral vector can have a partial or entire deletion of the adenoviral early region known as the E3 region, which is not essential for propagation of the adenoviral genome.

In one embodiment, the adenoviral vector is replication-deficient and requires, at most, complementation of the E1 region of the adenoviral genome, for propagation (e.g., to form adenoviral vector particles). Thus, the replication-deficient adenoviral vector requires complementation of at least one replication-essential gene function of the E1A subregion and/or the E1B subregion of the adenoviral genome (denoted an E1-deficient adenoviral vector) for propagation (e.g., to form adenoviral vector particles). The adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). Such an adenoviral vector requires, at most, complementation of a deficiency in the E1 region of the adenoviral genome for propagation.

In one embodiment, the adenoviral vector is replication-deficient and requires, at most, complementation of the E2 region, preferably the E2A subregion, of the adenoviral genome, for propagation (e.g., to form adenoviral vector particles). Thus, the replication-deficient adenoviral vector requires complementation of at least one replication-essential gene function of the E2A subregion of the adenoviral genome (denoted an E2A-deficient adenoviral vector) for propagation (e.g., to form adenoviral vector particles). The adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector). Such an adenoviral vector requires, at most, complementation of a deficiency in the E2 region of the adenoviral genome for propagation.

In one embodiment, the adenoviral vector is replication-deficient and requires, at most, complementation of the E4 region of the adenoviral genome, for propagation (e.g., to form adenoviral vector particles). Thus, the replication-deficient adenoviral vector requires complementation of at least one replication-essential gene function of the E4 region of the adenoviral genome (denoted an E4-deficient adenoviral vector) for propagation (e.g., to form adenoviral vector particles). The adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector). Such an adenoviral vector requires, at most, complementation of a deficiency in the E4 region of the adenoviral genome for propagation.

In one embodiment, the adenoviral vector requires complementation of the E1 and E2 (e.g., E2A) regions of the adenoviral genome for propagation (denoted an E1/E2-deficient adenoviral vector), wherein the adenoviral vector also can be deficient in at least one gene function of the E3 region (denoted an E1/E2/E3-deficient adenoviral vector). Such an adenoviral vector requires, at most, complementation of a deficiency in the E1 region and a deficiency in the E2 region of the adenoviral genome for propagation.

In one embodiment, the adenoviral vector is replication-deficient and requires, at most, complementation of the E1 and E4 regions of the adenoviral genome for propagation (e.g., to form adenoviral vector particles). Thus, the replication-deficient adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). Such an adenoviral vector requires, at most, complementation of a deficiency in the E1 region and a deficiency in the E4 region of the adenoviral genome for propagation.

In a preferred embodiment, the adenoviral vector requires, at most, complementation of a deficiency in the E1 region of the adenoviral genome for propagation, and does not require complementation of any other deficiency of the adenoviral genome for propagation. In another preferred embodiment, the adenoviral vector requires, at most, complementation of a deficiency in both the E1 and E4 regions of the adenoviral genome for propagation, and does not require complementation of any other deficiency of the adenoviral genome for propagation.

The adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

The replication-deficient adenoviral vector of the invention can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., *J. Gen. Virol.,* 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 1995/34671 and Brough et al., *J. Virol.,* 71: 9206-9213 (1997)). Other suitable complementing cell lines to produce the replication-deficient adenoviral vector of the invention include complementing cells that have been generated to propagate adenoviral vectors encoding transgenes whose expression inhibits viral growth in host cells (see, e.g., U.S. Patent Application Publication 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenoviral vector. Alternatively, the inventive adenoviral vector can comprise a non-native replication-essential gene that complements for the one or more replication-essential gene functions lacking in the inventive replication-deficient adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenoviral vector, or an adenovirus of a different species than the inventive adenoviral vector).

An example of an E1/E3-deficient serotype 28 adenoviral vector comprising a serotype 45 hexon protein and a serotype 45 fiber protein as described herein comprises the nucleic acid sequence of SEQ ID NO: 10. Using the publicly available genome information for Ad28, however, one of ordinary skill in the art would be able generate other Ad28 vectors with similar deficiencies and/or modifications using routine methods known in the art and/or described herein.

The adenoviral vector can further comprise one or more exogenous or non-native nucleic acids, which can be positioned at any suitable place in the adenoviral vector. By removing all or part of the adenoviral genome, for example, the E1, E3, and E4 regions of the adenoviral genome, the resulting adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome. In embodiments where the adenoviral vector comprises multiple exogenous nucleic acid sequences (e.g., 2, 3, 4 or more exogenous nucleic acid sequences), at least one exogenous nucleic acid sequence is positioned in the E1 region, and at least one exogenous nucleic acid sequence is positioned in the E4 region. For example, when the adenoviral vector comprises three exogenous nucleic acid sequences, two exogenous nucleic acid sequences can be positioned in the E1 region, and one exogenous nucleic acid sequence can be positioned in the E4 region.

An "exogenous" or "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the invention. The non-native nucleic acid sequence preferably is DNA and preferably encodes a protein (i.e., one or more nucleic acid sequences encoding one or more proteins).

The non-native nucleic acid can be in the form of a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenoviral vector can be used as a vaccine. For example, the non-native nucleic acid sequence can encode an antigen of a Herpes Simplex Virus-2, including, but not limited to an HSV-2 UL47 protein (e.g., SEQ ID NO: 11 or SEQ ID NO: 13), and/or an HSV-2 UL19 protein (e.g., SEQ ID NO: 12).

The invention provides a composition comprising the adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenoviral vector. Any suitable carrier can be used within the context of the invention, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. No. 6,225,289, U.S. Pat. No. 6,514,943, and International Patent Application Publication WO 2000/034444.

The composition also can be formulated to enhance transduction efficiency. In addition, one of ordinary skill in the art will appreciate that the adenoviral vector can be present in a composition with other therapeutic or biologically-active agents. For example, factors that control inflammation, such as ibuprofen or steroids, can be part of the composition to reduce swelling and inflammation associated with in vivo administration of the adenoviral vector. If the adenoviral vector is used to deliver an antigen-encoding nucleic acid sequence to a host, immune system stimulators or adjuvants, e.g., interleukins, lipopolysaccharide, double-stranded RNA, and/or TNFSF14/LIGHT (see, e.g., Zhang et al., *J. Virol. Methods,* 153(2): 142-148 (2008)) can be administered to enhance or modify any immune response to the antigen. Antibiotics, i.e., microbicides and fungicides, can be utilized to treat existing infection and/or reduce the risk of future infection, such as infection associated with gene transfer procedures.

The following examples further illustrate the invention but, of course, should not be construed as in any way limiting its scope.

Example 1

This example demonstrates the construction of a serotype 28 adenoviral vector comprising a serotype 45 adenovirus hexon protein and a serotype 45 adenovirus fiber protein, which encodes a Herpes Simplex Virus-2 (HSV) antigen.

A human serotype 28 adenoviral vector was prepared with a deletion in the E1 region, a portion of the hexon protein replaced with a portion of the hexon protein of a human serotype 45 adenovirus, and an insertion of a codon-optimized nucleic acid sequence encoding a wild-type HSV-2 UL19 protein into the E1 region (Ad28UL19 H(Ad45)). Ad28UL19 H(Ad45) is replication-deficient due to the deletion of the essential replication function provided by E1. In place of the E1 sequences, a CMVtetO UL19 expression cassette was introduced to provide the HSV-2 UL19 nucleic acid sequence. The expression cassette, located at the E1 region deletion junction, was oriented right-to-left with respect to the viral genome.

Ad28UL19 H(Ad45) has an E1 region deletion of nucleotides 462 through 3111. The deletion includes the E1A protein and part of the E1B protein, which renders the vector replication-incompetent in noncomplementing cell lines.

The construction of plasmid pAC28UL19.H(45) to provide Ad28UL19 H(Ad45) is schematically depicted in FIG. 1. Specifically, wild-type Ad28 virus DNA was rescued into a plasmid backbone by homologous recombination by using pAd28RSQ plasmid to make an Ad28 genome-containing plasmid (pACE28) (see FIG. 1, Step 3). A CMV tetO EGFP expression plasmid was introduced into the Ad28 genome-containing plasmid by homologous recombination to make an E1-deleted Ad28 genome-containing plasmid (pAC28EGFP) (462-3111 t ef) (see FIG. 1, Steps 4 and 5). PCR amplification and subcloning of the Ad45 hexon sequence into a shuttle plasmid was carried out by standard restriction enzyme subcloning. The Ad45 hexon nucleic acid sequence was inserted into pAC28EGFP plasmid by homologous recombination in *E. coli* to generate the Ad45 hexon-containing Ad28 adenoviral genome in plasmid form (pAC28EGFP.H(45)) (see FIG. 1, Steps 7 and 8). The HSV-2 UL19 gene was inserted into an adenoviral vector expression shuttle plasmid by standard restriction enzyme subcloning. The CMVTetO.UL19 gene was inserted into the pAC28EGFP.H(45) plasmid by homologous recombination in *E. coli* to generate the UL19-expressing Ad28 adenovector genome containing the Ad45 hexon sequence in plasmid form (pAC28UL19.H(45)) (see FIG. 1, Steps 9 and 10).

Plasmid pAC28UL19.H(45) was linearized with the restriction endonuclease PmeI. Adherent 293-ORF6 cells were transfected with the linearized plasmid, thereby resulting in conversion of the adenoviral genome (i.e., DNA) of the linearized plasmid into the viral vector Ad28UL19H(45).

The Ad28UL19H(45) adenoviral vector was expanded by serial passaging to generate high titer cell-virus lysate. The adenoviral vector was purified from the lysates by density-equilibrium centrifugation in cesium chloride gradients. The purified adenoviral vector was dialyzed into Final Formulation Buffer (FFB). The structural integrity of the genome of the adenoviral vector was confirmed by PCR, and the expression of the HSV-2 UL19 nucleic acid sequence was confirmed by Western blot.

A similar method was used to incorporate a portion of the Ad45 fiber nucleic acid sequence in place of a portion of the Ad28 fiber nucleic acid sequence.

The results of this example confirm the production of a serotype 28 adenoviral vector in accordance with the invention.

Example 2

This example demonstrates that the administration of the inventive serotype 28 adenoviral vector encoding one or more HSV antigens induces an immune response against HSV.

A serotype 28 adenoviral vector comprising portions of the hexon and fiber proteins from a serotype 45 adenovirus vector (Ad28 H/F) was produced using the methods described in Example 1. A first such adenoviral vector comprised a nucleic acid sequence encoding a wild-type HSV-2 UL47 protein (SEQ ID NO: 11). A second such adenoviral vector comprised a codon-optimized nucleic acid sequence encoding a wild-type HSV-2 UL19 protein (SEQ ID NO: 12).

T-cell response following a single intramuscular administration of each of the adenoviral vector-delivered antigens ($1\times10^9$ PU) was assessed in a mouse model and compared to natural infection ($1\times10^6$ PFU of HSV administered intravaginally) and control (i.e., formulation buffer (FFB)). A single administration of the adenoviral vector encoding either HSV-2 antigen induced a T-cell response that was greater than the T-cell response induced by a natural HSV infection.

The results of this example confirm that administration of the inventive serotype 28 adenoviral vector comprising a nucleic acid sequence encoding an HSV antigen induces an immune response against HSV.

Example 3

This example demonstrates that the administration of the inventive serotype 28 adenoviral vector encoding one or more HSV antigens induces an immune response against HSV.

Mice were divided into groups of four, and each group received a single intramuscular administration of one of the following: (a) an E1-deleted serotype 5 adenoviral vector encoding an HSV2 UL19 protein, (b) an E1-deleted serotype 28 adenoviral vector encoding an HSV2 UL19 protein, (c) the Ad28 H/F vector of the invention as described in Example 2, which encodes an HSV2 UL19 protein, and (d) formulation buffer (FFB; negative control). CD8+ T-cell responses following vaccination with the adenoviral vectors ($1\times10^9$ PU) were assessed. The elicited T-cell responses are plotted in the graph of FIG. 2.

As is apparent from the results depicted in FIG. 2, a single administration of the Ad28H/F vector elicited a strong CD8+ T-cell response that was comparable to the CD8+ T-cell response elicited by the Ad5 vector.

The results of this example confirm that administration of the inventive serotype 28 adenoviral vector can induce a strong immune response against HSV.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A replication-deficient serotype 28 adenoviral vector comprising chimeric hexon and fiber proteins selected from the group consisting of:

(a) a chimeric hexon protein comprising a portion of an adenovirus serotype 45 hexon protein in place of a corresponding portion of the endogenous serotype 28 hexon protein, wherein the portion of adenovirus serotype 45 hexon protein consists of the amino acid sequence of SEQ ID NO: 1 or an amino acid sequence that is at least 95% identical to SEQ ID NO: 1;

(b) a chimeric fiber protein comprising a portion of an adenovirus serotype 45 fiber protein in place of a corresponding portion of the endogenous serotype 28 fiber protein, wherein the portion of an adenovirus serotype 45 fiber protein consists of the amino acid sequence of SEQ ID NO: 3 or an amino acid sequence that is at least 95% identical to SEQ ID NO: 3; and (c) the chimeric hexon protein of (a) and the chimeric fiber protein of (b), wherein the adenoviral vector requires complementation of a deficiency in one or more early regions of the adenoviral genome for propagation and does not require complementation of any other deficiency of the adenoviral genome for propagation.

2. The replication-deficient serotype 28 adenoviral vector of claim 1, which comprises (c) the chimeric hexon protein of (a) and the chimeric fiber protein of (b).

3. The replication-deficient serotype 28 adenoviral vector of claim 1, wherein the portion of adenovirus serotype 45 hexon protein is encoded by the nucleic acid sequence of SEQ ID NO: 2.

4. The replication-deficient serotype 28 adenoviral vector of claim 1, wherein the portion of adenovirus serotype 45 fiber protein is encoded by the nucleic acid sequence of SEQ ID NO: 4.

5. The replication-deficient serotype 28 adenoviral vector of claim 1, which comprises:

(a) an amino acid sequence of a serotype 28 adenovirus penton protein, (b) an amino acid sequence of a serotype 28 adenovirus pIX protein, (c) an amino acid sequence of a serotype 28 adenovirus p100 protein, (d) an amino acid sequence of a serotype 28 adenovirus L1 52/55K protein, or (e) any combination of (a)-(d).

6. The replication-deficient serotype 28 adenoviral vector of claim 1, wherein the one or more early regions are selected from the group consisting of the E1 region, the E2 region, and the E4 region of the adenovirus genome.

7. The replication-deficient serotype 28 adenoviral vector of claim 6, wherein the adenoviral vector requires complementation of a deficiency in the E1 region of the adenoviral genome for propagation and does not require complementation of any other deficiency of the adenoviral genome for propagation.

8. The replication-deficient serotype 28 adenoviral vector of claim 6, wherein the adenoviral vector requires complementation of a deficiency in the E1A region or the E1B region of the adenoviral genome for propagation and does not require complementation of any other deficiency of the adenoviral genome for propagation.

9. The replication-deficient serotype 28 adenoviral vector of claim 6, wherein the adenoviral vector requires at most complementation of a deficiency in the E4 region of the adenoviral genome for propagation and does not require complementation of any other deficiency of the adenoviral genome for propagation.

10. The replication-deficient serotype 28 adenoviral vector of claim 6, wherein the adenoviral vector requires complementation of a deficiency in the E1 region of the adenoviral genome and a deficiency in the E4 region of the adenoviral genome for propagation and does not require complementation of any other deficiency of the adenoviral genome for propagation.

11. The replication-deficient serotype 28 adenoviral vector of claim 1, which comprises the nucleic acid sequence of SEQ ID NO: 10.

12. The replication-deficient serotype 28 adenoviral vector of claim 1 further comprising a transgene.

13. A composition comprising the replication-deficient serotype 28 adenoviral vector of claim 1 and a pharmaceutically acceptable carrier.

* * * * *

SEQUENCE LISTING

```
<160> NUMBER OF SEQ ID NOS: 13

<210> SEQ ID NO 1
<211> LENGTH: 531
<212> TYPE: PRT
<213> ORGANISM: Adenovirus

<400> SEQUENCE: 1

Arg Ser Gln Arg Leu Thr Leu Arg Phe Val Pro Val Asp Arg Glu Asp
1               5                   10                  15

Thr Thr Tyr Ser Tyr Lys Ala Arg Phe Thr Leu Ala Val Gly Asp Asn
            20                  25                  30

Arg Val Leu Asp Met Ala Ser Thr Tyr Phe Asp Ile Arg Gly Val Leu
        35                  40                  45

Asp Arg Gly Pro Ser Phe Lys Pro Tyr Ser Gly Thr Ala Tyr Asn Ser
    50                  55                  60

Leu Ala Pro Lys Ser Ala Pro Asn Pro Ser Gln Trp Asp Ala Lys Glu
65                  70                  75                  80

Lys Glu Gly Val Ala Gln Thr Glu Lys Asn Val Leu Lys Thr Phe Gly
                85                  90                  95

Val Ala Ala Thr Gly Gly Phe Asn Ile Thr Asp Gln Gly Leu Leu Leu
            100                 105                 110

Gly Thr Glu Glu Thr Ala Glu Asn Val Lys Lys Asp Ile Tyr Ala Glu
        115                 120                 125
```

```
Lys Thr Phe Gln Pro Glu Pro Gln Val Gly Glu Glu Asn Trp Gln Glu
    130                 135                 140

Ser Glu Ala Phe Tyr Gly Gly Arg Ala Ile Lys Lys Asp Thr Lys Met
145                 150                 155                 160

Lys Pro Cys Tyr Gly Ser Phe Ala Arg Pro Thr Asn Glu Lys Gly Gly
                165                 170                 175

Gln Ala Lys Phe Lys Thr Leu Asp Gly Gln Val Thr Lys Asp Pro Asp
            180                 185                 190

Ile Asp Phe Ala Tyr Phe Asp Val Pro Gly Gly Lys Ala Pro Thr Gly
        195                 200                 205

Ser Ser Leu Pro Glu Glu Tyr Lys Ala Asp Ile Ile Leu Tyr Thr Glu
    210                 215                 220

Asn Val Asn Leu Glu Thr Pro Asp Thr His Ile Val Tyr Lys Pro Gly
225                 230                 235                 240

Lys Glu Asp Asp Asn Ser Glu Ile Asn Leu Thr Gln Gln Ser Met Pro
                245                 250                 255

Asn Arg Pro Asn Tyr Ile Gly Phe Arg Asp Asn Phe Val Gly Leu Met
            260                 265                 270

Tyr Tyr Asn Ser Thr Gly Asn Met Gly Val Leu Ala Gly Gln Ala Ser
        275                 280                 285

Gln Leu Asn Ala Val Val Asp Leu Gln Asp Arg Asn Thr Glu Leu Ser
    290                 295                 300

Tyr Gln Leu Leu Leu Asp Ser Leu Gly Asp Arg Thr Arg Tyr Phe Ser
305                 310                 315                 320

Met Trp Asn Ser Ala Val Asp Ser Tyr Asp Pro Asp Val Arg Ile Ile
                325                 330                 335

Glu Asn His Gly Val Glu Asp Glu Leu Pro Asn Tyr Cys Phe Pro Leu
            340                 345                 350

Asn Gly Thr Gly Thr Asn Ser Thr Tyr Gln Gly Val Lys Ile Thr Gly
        355                 360                 365

Asn Asn Asp Gly Asp Leu Glu Thr Glu Trp Glu Arg Asp Glu Ala Ile
    370                 375                 380

Ser Arg Gln Asn Gln Ile Cys Lys Gly Asn Val Tyr Ala Met Glu Ile
385                 390                 395                 400

Asn Leu Gln Ala Asn Leu Trp Lys Ser Phe Leu Tyr Ser Asn Val Ala
                405                 410                 415

Leu Tyr Leu Pro Asp Ser Tyr Lys Tyr Thr Pro Ala Asn Val Thr Leu
            420                 425                 430

Pro Ala Asn Thr Asn Thr Tyr Glu Tyr Met Asn Gly Arg Val Val Ala
        435                 440                 445

Pro Ser Leu Val Asp Ala Tyr Ile Asn Ile Gly Ala Arg Trp Ser Leu
    450                 455                 460

Asp Pro Met Asp Asn Val Asn Pro Phe Asn His His Arg Asn Ala Gly
465                 470                 475                 480

Leu Arg Tyr Arg Ser Met Leu Leu Gly Asn Gly Arg Tyr Val Pro Phe
                485                 490                 495

His Ile Gln Val Pro Gln Lys Phe Phe Ala Ile Lys Asn Leu Leu Leu
            500                 505                 510

Leu Pro Gly Ser Tyr Thr Tyr Glu Trp Asn Phe Arg Lys Asp Val Asn
        515                 520                 525

Met Ile Leu
    530
```

<210> SEQ ID NO 2
<211> LENGTH: 1596
<212> TYPE: DNA
<213> ORGANISM: Adenovirus

<400> SEQUENCE: 2

```
ccggtcccag cgtctgacgc tgcgcttcgt gcccgtggat cgcgaggaca ccacgtactc     60

gtacaaggcg cgcttcactc tggccgtggg agacaaccgg gtgctagaca tggccagcac    120

ttactttgac atccgcggcg tcctggaccg cggtcccagc ttcaaaccct actcgggcac    180

ggcttacaac agcctggccc ccaagagcgc tcccaatccc agccagtggg atgcaaagga    240

aaaggaagga gttgcccaaa cagaaaaaaa tgttttaaaa acatttggtg ttgccgctac    300

aggtggtttt aatattacag atcagggttt gttacttgga actgaggaaa cagctgaaaa    360

cgttaaaaag gatatctatg cagagaaaac tttccagcct gaacctcaag ttggtgaaga    420

aaactggcag gaaagtgaag ccttttatgg aggaagggct attaagaaag acaccaaaat    480

gaagccatgc tatggttcat ttgccagacc cactaatgaa aaaggaggac aggctaaatt    540

taaaacacta gatgggcaag ttacaaaaga tccagatatt gactttgctt actttgacgt    600

ccctggcgga aaagctccaa caggcagtag tctaccggaa gaatacaaag cagatataat    660

tttgtacaca gaaaatgtta atctggaaac accagatact cacatagtgt ataaacctgg    720

caaagaagat gacaattctg aaattaactt aacacaacag tccatgccaa acagacccaa    780

ctacattggc tttagggaca actttgtagg tctcatgtac tacaacagta ctggcaacat    840

gggtgtgctg gctggtcagg cctctcagtt gaatgctgtg gtggacttgc aagacagaaa    900

caccgagctg tcttaccagc tcttgctaga ttctctgggt gacagaacca gatactttag    960

catgtggaac tctgcggttg acagttatga tcccgatgtc aggatcattg agaatcacgg   1020

tgtggaagat gaacttccaa actattgctt cccattgaat ggcactggta ccaattccac   1080

ctatcaaggt gtaaaaatta caggtaataa tgatggcgat cttgaaaccg aatgggaaag   1140

agatgaagca atctctagac aaaaccaaat ctgcaagggc aacgtctatg ccatggagat   1200

caacctccag gccaacctgt ggaagagttt tctgtactcg aacgtagccc tgtacctgcc   1260

tgactcatac aagtacacgc cggccaacgt cacgctgccc gccaacacca acacctacga   1320

gtacatgaac ggccgcgtgg tagccccctc gctggtggac gcttacatca acatcggcgc   1380

ccgctggtcg ctggatccca tggacaatgt aaacccattc aaccaccacc gcaacgcggg   1440

cctgcgctac cgttccatgt tgttgggcaa cggtcgctac gtgcccttcc acatccaagt   1500

gccccaaaag ttctttgcca tcaagaacct gcttctgctc ccgggctcct acacctacga   1560

gtggaacttc cgcaaggacg tcaacatgat cctgca                              1596
```

<210> SEQ ID NO 3
<211> LENGTH: 324
<212> TYPE: PRT
<213> ORGANISM: Adenovirus

<400> SEQUENCE: 3

```
Leu Ser Leu Lys Leu Ala Asp Pro Ile Ala Ile Val Asn Gly Asp Val
1               5                   10                  15

Ser Leu Lys Val Gly Gly Gly Leu Thr Leu Gln Glu Gly Asn Leu Thr
            20                  25                  30

Val Asp Ala Lys Ala Pro Leu Gln Val Ala Asn Asp Asn Lys Leu Glu
        35                  40                  45

Leu Ser Tyr Ala Asp Pro Phe Glu Val Lys Asp Thr Lys Leu Gln Leu
```

```
    50                  55                  60

Lys Val Gly His Gly Leu Lys Val Ile Asp Glu Lys Thr Ser Ser Gly
65                  70                  75                  80

Leu Gln Ser Leu Ile Gly Asn Leu Val Val Leu Thr Gly Lys Gly Ile
                85                  90                  95

Gly Thr Gln Glu Leu Lys Asp Lys Asp Asp Glu Thr Lys Asn Ile Gly
            100                 105                 110

Val Gly Ile Asn Val Arg Ile Gly Lys Asn Glu Ser Leu Ala Phe Asp
        115                 120                 125

Lys Asp Gly Asn Leu Val Ala Trp Asp Asn Glu Asn Asp Arg Arg Thr
    130                 135                 140

Leu Trp Thr Thr Pro Asp Thr Ser Pro Asn Cys Lys Ile Ser Thr Glu
145                 150                 155                 160

Lys Asp Ser Lys Leu Thr Leu Val Leu Thr Lys Cys Gly Ser Gln Ile
                165                 170                 175

Leu Ala Ser Val Ser Leu Leu Ala Val Ala Gly Ser Tyr Leu Asn Met
            180                 185                 190

Thr Ala Ser Thr Gln Lys Ser Ile Lys Val Ser Leu Met Phe Asp Ser
        195                 200                 205

Lys Gly Leu Leu Met Thr Thr Ser Ser Ile Asp Lys Gly Tyr Trp Asn
    210                 215                 220

Tyr Arg Asn Lys Asn Ser Val Val Gly Thr Ala Tyr Glu Asn Ala Ile
225                 230                 235                 240

Pro Phe Met Pro Asn Leu Val Ala Tyr Pro Arg Pro Asn Thr Pro Asp
                245                 250                 255

Ser Lys Ile Tyr Ala Arg Ser Lys Ile Val Gly Asn Val Tyr Leu Ala
            260                 265                 270

Gly Leu Ala Tyr Gln Pro Ile Val Ile Thr Val Ser Phe Asn Gln Glu
        275                 280                 285

Lys Asp Ala Ser Cys Ala Tyr Ser Ile Thr Phe Glu Phe Ala Trp Asn
    290                 295                 300

Lys Asp Tyr Val Gly Gln Phe Asp Thr Thr Ser Phe Thr Phe Ser Tyr
305                 310                 315                 320

Ile Ala Gln Glu
```

<210> SEQ ID NO 4
<211> LENGTH: 975
<212> TYPE: DNA
<213> ORGANISM: Adenovirus

<400> SEQUENCE: 4

```
ttgtcactca aactggctga cccaatagcc atcgtcaatg ggatgtctc actcaaggtg     60

ggaggtggac tcactttgca agaaggaaac ctaactgttg atgcaaaggc tccattgcaa    120

gttgcaaatg acaacaaatt ggagctttct tatgcagacc catttgaggt taaagacact    180

aagctacaat taaaagtagg tcatggttta aaagtaatag atgaaaaaac ttcttcaggt    240

cttcaaagtc taattggaaa tctcgtagtt ttaacaggaa aaggaattgg cactcaagaa    300

ttaaaagaca aagacgatga aactaaaaat ataggagttg gaataaatgt gagaataggg    360

aaaaacgaaa gtctggcgtt tgacaaagat ggaaatttgg tagcatggga taatgaaaac    420

gacaggcgca ctctatggac aactccagac acatctccaa attgtaaaat aagtactgaa    480

aaagactcca aacttacttt agtccttact aaatgcggat ctcaaattct agcaagtgtg    540

tctttgcttg ctgtcgctgg aagttatctt aatatgacag ctagtactca aaagagtata    600
```

```
aaggtatctt tgatgtttga ctcaaaaggg cttctaatga ctacatcttc tattgataaa    660

ggatattgga attatagaaa taaaaacagc gttgttggaa ctgcttatga aaacgcaatt    720

ccatttatgc caaatttagt ggcttatcca agacctaaca cgccagactc taaaatttat    780

gctagaagca aaattgttgg aaatgtttat ttagcaggtt tggcttacca accaattgtc    840

ataacagtta gttttaatca ggagaaggat gcaagttgtg cttactcaat aacatttgaa    900

tttgcctgga acaaagacta cgttggtcaa tttgatacca cctcctttac cttctcttat    960

attgcccaag aatga                                                     975
```

<210> SEQ ID NO 5
<211> LENGTH: 134
<212> TYPE: PRT
<213> ORGANISM: Adenovirus

<400> SEQUENCE: 5

```
Met Asn Gly Thr Gly Gly Pro Phe Glu Gly Gly Leu Phe Ser Pro Tyr
1               5                   10                  15

Leu Thr Thr Arg Leu Pro Gly Trp Ala Gly Val Arg Gln Asn Val Met
            20                  25                  30

Gly Ser Thr Val Asp Gly Arg Pro Val Leu Pro Ala Asn Ser Ser Thr
        35                  40                  45

Met Thr Tyr Ala Thr Val Gly Ser Ser Ser Leu Asp Ser Thr Ala Ala
    50                  55                  60

Ala Ala Ala Ala Ala Ala Ala Met Thr Ala Thr Arg Leu Ala Ser Ser
65                  70                  75                  80

Tyr Met Pro Ser Ser Gly Ser Ser Pro Ser Val Pro Ser Ser Ile Ile
                85                  90                  95

Ala Glu Glu Lys Leu Leu Ala Leu Leu Ala Glu Leu Glu Ala Leu Ser
            100                 105                 110

Arg Gln Leu Ala Ala Leu Thr Gln Gln Val Ser Glu Leu Arg Glu Gln
        115                 120                 125

Gln Gln Gln Gln Asn Lys
    130
```

<210> SEQ ID NO 6
<211> LENGTH: 519
<212> TYPE: PRT
<213> ORGANISM: Adenovirus

<400> SEQUENCE: 6

```
Met Arg Arg Ala Val Val Ser Ser Ser Pro Pro Pro Ser Tyr Glu Ser
1               5                   10                  15

Val Met Ala Gln Ala Thr Leu Glu Val Pro Phe Val Pro Pro Arg Tyr
            20                  25                  30

Met Ala Pro Thr Glu Gly Arg Asn Ser Ile Arg Tyr Ser Glu Leu Ala
        35                  40                  45

Pro Gln Tyr Asp Thr Thr Arg Val Tyr Leu Val Asp Asn Lys Ser Ala
    50                  55                  60

Asp Ile Ala Ser Leu Asn Tyr Gln Asn Asp His Ser Asn Phe Leu Thr
65                  70                  75                  80

Thr Val Val Gln Asn Asn Asp Phe Thr Pro Ala Glu Ala Ser Thr Gln
                85                  90                  95

Thr Ile Asn Phe Asp Glu Arg Ser Arg Trp Gly Gly Asp Leu Lys Thr
            100                 105                 110
```

-continued

```
Ile Leu His Thr Asn Met Pro Asn Val Asn Glu Tyr Met Phe Thr Ser
        115                 120                 125

Lys Phe Lys Ala Arg Val Met Val Ala Arg Lys His Pro Lys Asp Val
    130                 135                 140

Asp Ala Ser Asp Leu Ser Lys Asp Ile Leu Glu Tyr Asp Trp Phe Glu
145                 150                 155                 160

Phe Thr Leu Pro Glu Gly Asn Phe Ser Glu Thr Met Thr Ile Asp Leu
                165                 170                 175

Met Asn Asn Ala Ile Leu Glu Asn Tyr Leu Gln Val Gly Arg Gln Asn
            180                 185                 190

Gly Val Leu Glu Ser Asp Ile Gly Val Lys Phe Asp Ser Arg Asn Phe
        195                 200                 205

Lys Leu Gly Trp Asp Pro Val Thr Lys Leu Val Met Pro Gly Val Tyr
    210                 215                 220

Thr Tyr Glu Ala Phe His Pro Asp Val Val Leu Leu Pro Gly Cys Gly
225                 230                 235                 240

Val Asp Phe Thr Glu Ser Arg Leu Ser Asn Leu Leu Gly Ile Arg Lys
                245                 250                 255

Lys Gln Pro Phe Gln Glu Gly Phe Arg Ile Met Tyr Glu Asp Leu Val
            260                 265                 270

Gly Gly Asn Ile Pro Ala Leu Leu Asn Val Lys Glu Tyr Leu Lys Asp
        275                 280                 285

Lys Glu Glu Ala Gly Thr Ala Asp Ala Asn Thr Ile Lys Ala Gln Asn
    290                 295                 300

Asp Ala Val Pro Arg Gly Asp Asn Tyr Ala Ser Ala Ala Glu Ala Lys
305                 310                 315                 320

Ala Ala Gly Lys Glu Ile Glu Leu Lys Ala Ile Leu Lys Asp Asp Ser
                325                 330                 335

Asn Arg Ser Tyr Asn Val Ile Glu Gly Thr Thr Asp Thr Leu Tyr Arg
            340                 345                 350

Ser Trp Tyr Leu Ser Tyr Thr Tyr Gly Asp Pro Glu Lys Gly Val Gln
        355                 360                 365

Ser Trp Thr Leu Leu Thr Thr Pro Asp Val Thr Cys Gly Ala Glu Gln
    370                 375                 380

Val Tyr Trp Ser Leu Pro Asp Leu Met Gln Asp Pro Val Thr Phe Arg
385                 390                 395                 400

Ser Thr Gln Gln Val Ser Asn Tyr Pro Val Val Gly Ala Glu Leu Met
                405                 410                 415

Pro Phe Arg Ala Lys Ser Phe Tyr Asn Asp Leu Ala Val Tyr Ser Gln
            420                 425                 430

Leu Ile Arg Ser Tyr Thr Ser Leu Thr His Val Phe Asn Arg Phe Pro
        435                 440                 445

Asp Asn Gln Ile Leu Cys Arg Pro Pro Ala Pro Thr Ile Thr Thr Val
    450                 455                 460

Ser Glu Asn Val Pro Ala Leu Thr Asp His Gly Thr Leu Pro Leu Arg
465                 470                 475                 480

Ser Ser Ile Arg Gly Val Gln Arg Val Thr Val Thr Asp Ala Arg Arg
                485                 490                 495

Arg Thr Cys Pro Tyr Val Tyr Lys Ala Leu Gly Ile Val Ala Pro Arg
            500                 505                 510

Val Leu Ser Ser Arg Thr Phe
        515
```

<210> SEQ ID NO 7
<211> LENGTH: 732
<212> TYPE: PRT
<213> ORGANISM: Adenovirus

<400> SEQUENCE: 7

```
Met Glu Glu Gln Pro Arg Lys Gln Glu Gln Glu Glu Asp Leu Thr Thr
1               5                   10                  15

His Glu Gln Pro Lys Ile Glu Gln Asp Leu Gly Phe Glu Glu Pro Ala
            20                  25                  30

Arg Leu Glu Pro Pro Gln Asp Glu Gln Glu His Glu Gln Asp Ala Gly
        35                  40                  45

Gln Glu Glu Thr Asp Ala Gly Leu Glu His Gly Tyr Leu Gly Gly Glu
    50                  55                  60

Glu Asp Val Leu Leu Lys His Leu Gln Arg Gln Ser Leu Ile Leu Arg
65                  70                  75                  80

Asp Ala Leu Ala Asp Arg Ser Glu Thr Pro Leu Ser Val Glu Glu Leu
                85                  90                  95

Cys Arg Ala Tyr Glu Leu Asn Leu Phe Ser Pro Arg Val Pro Pro Lys
            100                 105                 110

Arg Gln Pro Asn Gly Thr Cys Glu Pro Asn Pro Arg Leu Asn Phe Tyr
        115                 120                 125

Pro Val Phe Ala Val Pro Glu Ala Leu Ala Thr Tyr His Ile Phe Phe
    130                 135                 140

Lys Asn Gln Lys Ile Pro Val Ser Cys Arg Ala Asn Arg Thr Arg Ala
145                 150                 155                 160

Asp Ala Leu Leu Ala Leu Gly Pro Gly Ala His Ile Pro Asp Ile Ala
                165                 170                 175

Ser Leu Glu Glu Val Pro Lys Ile Phe Glu Gly Leu Gly Arg Asp Glu
            180                 185                 190

Thr Arg Ala Ala Asn Ala Leu Lys Glu Thr Ala Glu Glu Glu Gly His
        195                 200                 205

Thr Ser Ala Leu Val Glu Leu Glu Gly Asp Asn Ala Arg Leu Ala Val
    210                 215                 220

Leu Lys Arg Ser Val Glu Leu Thr His Phe Ala Tyr Pro Ala Val Asn
225                 230                 235                 240

Leu Pro Pro Lys Val Met Arg Arg Ile Met Asp Gln Leu Ile Met Pro
                245                 250                 255

His Ile Glu Ala Leu Asp Glu Ser Gln Glu Gln Arg Pro Glu Asp Val
            260                 265                 270

Arg Pro Val Val Ser Asp Glu Met Leu Ala Arg Trp Leu Gly Thr Arg
        275                 280                 285

Asp Pro Gln Ala Leu Glu Gln Arg Arg Lys Leu Met Leu Ala Val Val
    290                 295                 300

Leu Val Thr Leu Glu Leu Glu Cys Met Arg Arg Phe Phe Ser Asp Pro
305                 310                 315                 320

Glu Thr Leu Arg Lys Val Glu Glu Thr Leu His Tyr Thr Phe Arg His
                325                 330                 335

Gly Phe Val Arg Gln Ala Cys Lys Ile Ser Asn Val Glu Leu Thr Asn
            340                 345                 350

Leu Val Ser Cys Leu Gly Ile Leu His Glu Asn Arg Leu Gly Gln Thr
        355                 360                 365

Val Leu His Ser Thr Leu Lys Gly Glu Ala Arg Arg Asp Tyr Val Arg
    370                 375                 380
```

```
Asp Cys Ile Phe Leu Phe Leu Cys His Thr Trp Gln Ala Ala Met Gly
385                 390                 395                 400

Val Trp Gln Gln Cys Leu Glu Asp Glu Asn Leu Lys Glu Leu Asp Lys
                405                 410                 415

Val Leu Ala Arg Asn Leu Lys Lys Leu Trp Thr Gly Phe Asp Glu Arg
            420                 425                 430

Thr Val Ala Ser Asp Leu Ala Gln Ile Val Phe Pro Glu Arg Leu Arg
        435                 440                 445

Gln Thr Leu Lys Gly Gly Leu Pro Asp Phe Met Ser Gln Ser Met Ile
    450                 455                 460

Gln Asn Tyr Arg Thr Phe Ile Leu Glu Arg Ser Gly Met Leu Pro Ala
465                 470                 475                 480

Thr Cys Asn Ala Phe Pro Ser Asp Phe Val Pro Leu Ser Tyr Arg Glu
                485                 490                 495

Cys Pro Pro Pro Leu Trp Ser His Cys Tyr Leu Leu Gln Leu Ala Asn
            500                 505                 510

Tyr Ile Ala Tyr His Ser Asp Val Ile Glu Asp Val Ser Gly Glu Gly
        515                 520                 525

Leu Leu Glu Cys His Cys Arg Cys Asn Leu Cys Ser Pro His Arg Ser
    530                 535                 540

Leu Val Cys Asn Pro Gln Leu Leu Ser Glu Thr Gln Val Ile Gly Thr
545                 550                 555                 560

Phe Glu Leu Gln Gly Pro Gln Glu Ser Thr Ala Pro Leu Lys Leu Thr
                565                 570                 575

Pro Gly Leu Trp Thr Ser Ala Tyr Leu Arg Lys Phe Val Pro Glu Asp
            580                 585                 590

Tyr His Ala His Glu Ile Lys Phe Phe Glu Asp Gln Ser Arg Pro Gln
        595                 600                 605

His Ala Asp Leu Thr Ala Cys Val Ile Thr Gln Gly Ala Ile Leu Ala
    610                 615                 620

Gln Leu His Ala Ile Gln Lys Ser Arg Gln Glu Phe Leu Leu Lys Lys
625                 630                 635                 640

Gly Arg Gly Val Tyr Leu Asp Pro Gln Thr Gly Glu Val Leu Asn Pro
                645                 650                 655

Gly Leu Pro Gln His Ala Glu Glu Glu Ala Gly Ala Ala Ser Gly Gly
            660                 665                 670

Asp Gly Arg Arg Met Gly Gln Pro Gly Arg Gly Gly Arg Met Gly Gly
        675                 680                 685

Gly Asp Arg Gly Gly Arg Ile Gly Arg Gly Gly Arg Gly Ala Gly Asn
    690                 695                 700

Arg Ala Ala Arg Arg Arg Thr Ile Arg Ala Gly Ser Pro Gly Gly His
705                 710                 715                 720

Gly Tyr Asn Leu Arg Ser Ser Gly Gln Ala Ser Ser
                725                 730


<210> SEQ ID NO 8
<211> LENGTH: 373
<212> TYPE: PRT
<213> ORGANISM: Adenovirus

<400> SEQUENCE: 8

Met His Pro Val Leu Arg Gln Met Arg Pro Thr Pro Pro Ala Thr Thr
1               5                   10                  15

Ala Thr Ala Ala Val Ala Gly Ala Gly Ala Val Ala Pro Pro Gln Thr
            20                  25                  30
```

```
Glu Met Asp Leu Glu Glu Gly Glu Gly Leu Ala Arg Leu Gly Ala Pro
        35                  40                  45

Ser Pro Glu Arg His Pro Arg Val Gln Leu Gln Lys Asp Val Arg Pro
    50                  55                  60

Ala Tyr Val Pro Pro Gln Asn Leu Phe Arg Asp Arg Ser Gly Glu Glu
65                  70                  75                  80

Pro Glu Glu Met Arg Asp Cys Arg Phe Arg Ala Gly Arg Glu Leu Arg
                85                  90                  95

Glu Gly Leu Asp Arg Gln Arg Val Leu Arg Asp Glu Asp Phe Glu Pro
            100                 105                 110

Asn Glu Gln Thr Gly Ile Ser Pro Ala Arg Ala His Val Ala Ala Ala
        115                 120                 125

Asn Leu Val Thr Ala Tyr Glu Gln Thr Val Lys Gln Glu Arg Asn Phe
    130                 135                 140

Gln Lys Ser Phe Asn Asn His Val Arg Thr Leu Ile Ala Arg Glu Glu
145                 150                 155                 160

Val Ala Leu Gly Leu Met His Leu Trp Asp Leu Ala Glu Ala Ile Val
                165                 170                 175

Gln Asn Pro Asp Ser Lys Pro Leu Thr Ala Gln Leu Phe Leu Val Val
            180                 185                 190

Gln His Ser Arg Asp Asn Glu Ala Phe Arg Glu Ala Leu Leu Asn Ile
        195                 200                 205

Ala Glu Pro Glu Gly Arg Trp Leu Leu Glu Leu Ile Asn Ile Leu Gln
    210                 215                 220

Ser Ile Val Val Gln Glu Arg Ser Leu Ser Leu Ala Glu Lys Val Ala
225                 230                 235                 240

Ala Ile Asn Tyr Ser Val Leu Ser Leu Gly Lys Phe Tyr Ala Arg Lys
                245                 250                 255

Ile Tyr Lys Thr Pro Tyr Val Pro Ile Asp Lys Glu Val Lys Ile Asp
            260                 265                 270

Ser Phe Tyr Met Arg Met Ala Leu Lys Val Leu Thr Leu Ser Asp Asp
        275                 280                 285

Leu Gly Val Tyr Arg Asn Asp Arg Ile His Lys Ala Val Ser Thr Ser
    290                 295                 300

Arg Arg Arg Glu Leu Ser Asp Arg Glu Leu Met Leu Ser Leu Arg Arg
305                 310                 315                 320

Ala Leu Val Gly Gly Ala Ala Gly Gly Glu Glu Ser Tyr Phe Asp Met
                325                 330                 335

Gly Ala Asp Leu His Trp Gln Pro Ser Arg Arg Ala Leu Glu Ala Ala
            340                 345                 350

Tyr Gly Pro Glu Asp Leu Glu Glu Asp Glu Glu Glu Glu Glu Asp Ala
        355                 360                 365

Pro Ala Ala Gly Tyr
    370


<210> SEQ ID NO 9
<211> LENGTH: 3531
<212> TYPE: DNA
<213> ORGANISM: Adenovirus

<400> SEQUENCE: 9

atggccttgg ttcaaagtca cggggccagt ggtcttcacg cagaggcggc agatccagga      60

tgtcaaccga cgcgtcgtcg cgcacgccag cgctctcagg gcgcagcacc gggacctgcc     120
```

-continued

```
cgagcgccac gccgacgtgc ctctgccgcc cctgcccgcg gggccggaac cgccgctgcc    180

gccgggagcg cgtccgcgac accgcttcta aaagcgcacc gcggcacggt cgtggccccg    240

cgcagctacg ggctcatgca atgcgtggac acggccacca actcacccgt agaaatcaag    300

taccatctgc atctcaagca cgccctcacc cgcctctacg aggtcaacct cagaaccctg    360

cccccggacc tggatctccg cgacaccatg gacagctccc aactgcgcgc cctcgtcttc    420

gctctccgcc cccgccgcgc cgagatctgg acctggctcc cgcgcgggct cgtcagcctc    480

tccgtcctcg aggagcccca gggtgagtcc cacgcaggcg aacatgaaaa ccaccagcca    540

gggccgccac tcctgaagtt cctcctcaag ggacgcgctg tgtatctcgt ggatgaggta    600

cagcccgtgc agcgctgcga gtactgcgga cgcttttaca agcatcagca cgagtgctcg    660

gttcgccggc gggatttcta ctttcatcac atcaacagcc actcgtccaa ctggtggcag    720

gaaatccagt tcttcccaat cggctctcat cctcgcacgg agaggctctt tgtcacctac    780

gatgtagaaa cctacacctg gatggggtcc ttcggcaagc agctcgtccc cttcatgctg    840

gtcatgaaat tctccgggga ccccgagctg atcgccctgg ctcgcgatct cgccgtgcgc    900

ttacgctggg atcgctggga gcgggacccc ctcaccttct actgcgtcac accagaaaag    960

atggccgtgg gccagcagtt ccgcctcttt cgcgacgagc tccagaccct catggcccgc   1020

gagctctggg cttccttcat gcaagccaac ccacatctcc aggagtgggc gctcgagcag   1080

cacggcctgc aatgccccga ggacctcacc tacgaggagc tcaaaaagct gccgcacatc   1140

aaaggccgcc cgcgattcat ggaactctac atcgtcgggc acaacatcaa cggcttcgac   1200

gagatcgtcc tcgccgccca ggtgatcaac aaccgagcct ccgtcccggg ccctttccgc   1260

atcacccgca atttcatgcc gcgggcaggc aagattctct tcaatgacgt cactttcgct   1320

ctgcctaacc ccctctcgaa gaagcgcacc gatttcgagc tctgggagca cggcggctgc   1380

gacgactcgg acttcaagta ccagttcttg aaagtcatgg tcagggacac cttcgccctg   1440

acgcacacct cgctccgcaa ggccgctcaa gcttacgccc tccccgtgga gaagggctgc   1500

tgtccctaca aggccgtgaa ccatttctac atgctgggct cttaccgtgc ggacgatcga   1560

ggattcccgc tccgggagta ctggaaggat gacgaggagt acgccctcaa ccgcgagctg   1620

tgggagaaga aaggagaagc gggttatgac atcatccgcg aaacgctgga ctactgcgcc   1680

atggacgtcc tcgtcaccgc cgagctcgtc gccaagctgc aagactccta cgcgcacttc   1740

atccgcgact cggtccgcct gccccacgcc cactttaaca tcttccaacg gcccaccatc   1800

tcctccaact cgcacgccat ctttcgccag atcgtcttcc gcgccgagca gccccagcgc   1860

accaatctcg gcccctcctt cttggccccc tcgcacgagt tgtatgacta cgtgcgcgcc   1920

agcatccgcg gggggcgctg ttatcccacc tacatcggca tcctctcgga gcccatctat   1980

gtctatgaca tctgcggcat gtacgcctcc gccctcacgc atcccatgcc ctggggtccg   2040

cccctcaacc cctacgagcg agcgctggcc gcccgcgagt ggcagatggc cttggatgat   2100

gcatcctcaa aaatcgatta ttttgacaag gaactctgtc cgggcatctt caccatcgat   2160

gcggaccccc ctgacgagca cctcctggat gtgctgcccc cgttctgctc gcgcaagggt   2220

ggcagactct gctggaccaa cgagcccctg cgcggcgagg tggccaccag cgtggacctg   2280

gtcaccctgc ataaccgcgg ctggcgcgtc aggatcgtgc ccgacgagcg caccaccgtc   2340

ttccccgaat ggaagtgcgt cgcgcgcgag tatgtccagc tcaacatcgc ggccaaggag   2400

cgcgccgacc gtgacaaaaa tcagaccatg agatccatcg ccaagcttct ctccaacgcc   2460

ctctatggct cctttgccac caagcttgac aataaaaaaa tagtcttttc tgaccagatg   2520
```

```
gatgaaagtc tcctaaaaag catcgcggca gggcaagcca acatcaaatc ctcctcgttt   2580

ctagaaactg acaacctgag tgccgaggtc atgcccgctc tcgagaggga atacctaccc   2640

caacagctgg cgctcgtgga cagcgacgcg gaagagagtg aggacgagca cagacccgcc   2700

ccttttata ccccccgtc ggggaccccc ggtcacgtgg cctacaccta caagccaatc   2760

accttcttgg atgcggagga gggggacatg tgcttgcaca cggtggaaaa ggtggacccc   2820

ctggtggaca acgaccgcta cccctcgcac gtggcctcct ttgtcttggc gtggacgcgc   2880

gccttcgtct cagagtggtc cgaatttctc tacgaggagg accgcgggac gcccctgcag   2940

gacaggccaa tcaagtccat ctacggggac accgacagcc tgtttgtcac cgagcgcgga   3000

cacagactca tggagacgcg aggtaagaag cgcatcaaaa agaacggggg aaaactggtt   3060

tttgaccccg aacaacccga gctcacctgg ctcgtcgagt gcgagaccgt ctgcgcccac   3120

tgcggagcgg acgcgttcgc ccccgagtcc gtctttctcg cacccaagct atacgccctg   3180

caatccctcc tctgtcccgc ctgtgggcgc tcttccaagg gcaagctccg cgccaagggc   3240

cacgccgccg aggccctcaa ctacgagctc atggtcaact gctatctcgc cgacgcgcag   3300

ggcgaagacc gtgcccgttt cagcaccagc aggatgagtc tcaagcgaac ccttgcaagc   3360

gcccagcccg gggcccaccc cttcaccgtg acggagacaa ccctcacgcg gaccctgaga   3420

ccctggaagg acatgacgct ggccgcgctg gacgcccatc gtctcgtgcc ctacagtcgc   3480

agtcgtccca acccccgaaa cgaggaagtc tgctggatcg agatgccgta g            3531
```

```
<210> SEQ ID NO 10
<211> LENGTH: 28607
<212> TYPE: DNA
<213> ORGANISM: Artificial Sequence
<220> FEATURE:
<223> OTHER INFORMATION: Synthetic

<400> SEQUENCE: 10

catcatcaat aatatacccc acaaagtaaa caaaagttaa tatgcaaatg agcttttgaa     60

tttagggcgg ggccgtcgct gattggccgt tgcaagaacc gttagtgacg tcacgacgca    120

cggccgacgc tcgccgcgga ggcgtggcct agcccggaag caagtcgcgg ggctgatgac    180

gtataaaaaa gcggacttta gacccggaaa cggccgattt tcccgcggcc acgcccggat    240

atgaggtaat tctgggcgga tgcaagtgaa attaggtcat tttggcgcga aaactgaatg    300

aggaagtgaa aagcgaaaaa taccggtccc tcccagggcg gaatatttac cgagggccga    360

gagactttga ccgattacgt ggggtttcg attgcggtgt ttttttcgcg aatttccgcg    420

tccgtgtcaa agtccggtgt ttatgtcaca gatcagctga tagctgctgt tggagaacga    480

tgccttctcc agggtgaacc tgaacggcat ctttgacatg gatgtctcgg tgtacaagat    540

cctgagatac gatgagacca agtccagggt gcgcgcttgc gagtgcgggg gcagacacac    600

caggatgcag ccagtggccc tggatgtgac cgaggagctg agaccagacc acctggtgat    660

ggcctgtacc gggaccgagt tcagctccag tggggaggac acagattaga ggtaggtttt    720

tgagtagtgg gcgtggctaa tgtgagtata aaggtgggtg tcttacgagg gtctttttgc    780

ttttctgcag acatcatgaa cgggaccggc gggcccttcg aagggggggct ttttagccct    840

tatttgacaa cccgcctgcc gggatgggcc ggagttcgtc agaatgtgat gggatcgacg    900

gtggatgggc gcccagtgct tccagcaaat tcctcgacca tgacctacgc gaccgtgggg    960

agctcgtcgc tcgacagcac cgccgcagcc gcggcagccg cagccgccat gacagcgacg   1020
```

-continued

```
agactggcct cgagctacat gcccagcagc ggcagcagcc cctctgtgcc cagttccatc   1080

atcgccgagg agaaactgct ggccctgctg gccgagctgg aagccctgag ccgccagctg   1140

gccgccctga cccagcaggt gtctgagctc cgcgagcagc agcagcagca aaataaatga   1200

ttcaataaac acagattctg attcaaacag caaagcatct ttattattta tttttcgcg    1260

cgcggtaggc cctggtccac ctctcccgat cattgagagt gcggtggatt ttttccagga   1320

cccggtagag gtgggattgg atgttgaggt acatgggcat gagcccgtcc cgggggtgga   1380

ggtagcacca ctgcatggcc tcgtgctctg gggtcgtgtt gtagatgatc cagtcatagc   1440

aggggcgctg ggcgtggtgc tggatgatgt ctttaaggag gagactgatg gccacgggga   1500

gccccttggt gtaggtgttg gcaaagcggt tgagctggga aggatgcatg cggggggaga   1560

tgatgtgcag tttggcctgg atcttgaggt tggcaatgtt gccgcccaga tcccgcctgg   1620

ggttcatgtt gtgcaggacc accaggacgg tgtagcccgt gcacttgggg aacttatcat   1680

gcaacttgga agggaatgcg tggaagaatt tggagacgcc cttgtgcccg cccaggtttt   1740

ccatgcactc atccatgatg atggcgatgg gcccgtgggc tgcggctttg gcaaagacgt   1800

ttctggggtc agagacatcg taattatgct cctgggtgag atcgtcataa gacattttaa   1860

tgaatttggg gcggagggtg ccagattggg ggacgatggt tccctcgggc cccggggcga   1920

agttcccctc gcagatctgc atctcccagg ctttcatctc ggaggggggg atcatgtcca   1980

cctgcggggc tatgaaaaaa acggtttccg gggcgggggt gatgagctgc gaggagagca   2040

ggtttcttaa cagctgggac ttgccgcacc cggtcgggcc gtatatgacc ccgatgacgg   2100

gttgcaggtg gtagttcaag gacatgcagc tgccgtcgtc ccggaggagg ggggccacct   2160

cgttgagcat gtctctgact tggaggtttt cccggacgag ctcgccgagg aggcggtccc   2220

cgcccagcga gagcagctct tgcagggaag caaagttttt caggggcttg agcccgtcgg   2280

ccatgggcat cttggcgagg gtctgcgaga ggagctccag gcggtcccag agctcggtga   2340

cgtgctctac ggcatctcga tccagcagac ttcctcgttt cgggggttgg gacgactgcg   2400

actgtagggc acgagacgat gggcgtccag cgcggccagc gtcatgtcct tccagggtct   2460

cagggtccgc gtgagggttg tctccgtcac ggtgaagggg tgggccccgg gctgggcgct   2520

tgcaagggtt cgcttgagac tcatcctgct ggtgctgaaa cgggcacggt cttcgccctg   2580

cgcgtcggcg agatagcagt tgaccatgag ctcgtagttg agggcctcgg cggcgtggcc   2640

cttggcgcgg agcttgccct tggaagagcg cccacaggcg ggacagagga gggattgcag   2700

ggcgtatagc ttgggtgcga gaaagacgga ctcgggggcg aacgcgtccg ctccgcagtg   2760

ggcgcagacg gtctcgcact cgacgagcca ggtgagctcg ggttgttcgg ggtcaaaaac   2820

cagttttccc ccgttctttt tgatgcgctt cttacctcgc gtctccatga gtctgtgtcc   2880

gcgctcggtg acaaacaggc tgtcggtgtc cccgtagatg gacttgattg gcctgtcctg   2940

caggggcgtc ccgcggtcct cctcgtagag aaattcggac cactctgaga cgaaggcgcg   3000

cgtccacgcc aagacaaagg aggccacgtg cgaggggtag cggtcgttgt ccaccagggg   3060

gtccaccttt tccaccgtgt gcaagcacat gtcccccctcc tccgcatcca agaaggtgat  3120

tggcttgtag gtgtaggcca cgtgaccggg ggtccccgac ggggggtat aaaagggggc    3180

gggtctgtgc tcgtcctcac tctcttccgc gtcgctgtcc acgagcgcca gctgttgggg   3240

taggtattcc ctctcgagag cgggcatgac ctcggcactc aggttgtcag tttctagaaa   3300

cgaggaggat ttgatgttgg cttgccctgc cgcgatgctt tttaggagac tttcatccat   3360

ctggtcagaa aagactattt ttttattgtc aagcttggtg gcaaaggagc catagagggc   3420
```

```
gttggagaga agcttggcga tggatctcat ggtctgattt ttgtcacggt cggcgcgctc   3480
cttggccgcg atgttgagct ggacatactc gcgcgcgacg cacttccatt cggggaagac   3540
ggtggtgcgc tcgtcgggca cgatcctgac gcgccagccg cggttatgca gggtgaccag   3600
gtccacgctg gtggccacct cgccgcgcag gggctcgttg gtccagcaga gtctgccacc   3660
cttgcgcgag cagaacgggg gcagcacatc caggaggtgc tcgtcagggg ggtccgcatc   3720
gatggtgaag atgcccggac agagttcctt gtcaaaataa tcgatttttg aggatgcatc   3780
atccaaggcc atctgccact cgcgggcggc cagcgctcgc tcgtaggggt tgaggggcgg   3840
accccagggc atgggatgcg tgagggcgga ggcgtacatg ccgcagatgt catagacata   3900
gatgggctcc gagaggatgc cgatgtaggt gggataacag cgcccccgc ggatgctggc    3960
gcgcacgtag tcatacaact cgtgcgaggg ggccaagaag gaggggccga gattggtgcg   4020
ctggggctgc tcggcgcgga agacgatctg gcgaaagatg gcgtgcgagt tggaggagat   4080
ggtgggccgt tggaagatgt taaagtgggc gtggggcagg cggaccgagt cgcggatgaa   4140
gtgcgcgtag gagtcttgca gcttggcgac gagctcggcg gtgacgagga cgtccatggc   4200
gcagtagtcc agcgtttcgc ggatgatgtc ataacccgct tctcctttct tctcccacag   4260
ctcgcggttg agggcgtact cctcgtcatc cttccagtac tcccggagcg ggaatcctcg   4320
atcgtccgca cggtaagagc ccagcatgta gaaatggttc acggccttgt agggacagca   4380
gcccttctcc acggggaggg cgtaagcttg agcggccttg cggagcgagg tgtgcgtcag   4440
ggcgaaggtg tccctgacca tgactttcaa gaactggtac ttgaagtccg agtcgtcgca   4500
gccgccgtgc tcccagagct cgaaatcggt gcgcttcttc gagagggggt taggcagagc   4560
gaaagtgacg tcattgaaga gaatcttgcc tgcccgcggc atgaaattgc gggtgatgcg   4620
gaaagggccc gggacggagg ctcggttgtt gatcacctgg gcggcgagga cgatctcgtc   4680
gaagccgttg atgttgtgcc cgacgatgta gagttccatg aatcgcgggc ggcctttgat   4740
gtgcggcagc tttttgagct cctcgtaggt gaggtcctcg gggcattgca ggccgtgctg   4800
ctcgagcgcc cactcctgga gatgtgggtt ggcttgcatg aaggaagccc agagctcgcg   4860
ggccatgagg gtctggagct cgtcgcgaaa gaggcggaac tgctggccca cggccatctt   4920
ttctggtgtg acgcagtaga aggtgagggg gtcccgctcc cagcgatccc agcgtaagcg   4980
cacggcgaga tcgcgagcca gggcgatcag ctcggggtcc ccggagaatt tcatgaccag   5040
catgaagggg acgagctgct tgccgaagga ccccatccag gtgtaggttt ctacatcgta   5100
ggtgacaaag agcctctccg tgcgaggatg agagccgatt gggaagaact ggatttcctg   5160
ccaccagttg gacgagtggc tgttgatgtg atgaaagtag aaatcccgcc ggcgaaccga   5220
gcactcgtgc tgatgcttgt aaaagcgtcc gcagtactcg cagcgctgca cgggctgtac   5280
ctcatccacg agatacacag cgcgtccctt gaggaggaac ttcaggagtg gcggccctgg   5340
ctggtggttt tcatgttcgc ctgcgtggga ctcaccctgg ggctcctcga ggacggagag   5400
gctgacgagc ccgcgcggga gccaggtcca gatctcggcg cggcgggggc ggagagcgaa   5460
gacgagggcg cgcagttggg agctgtccat ggtgtcgcgg agatccaggt ccgggggcag   5520
ggttctgagg ttgacctcgt agaggcgggt gagggcgtgc ttgagatgca gatggtactt   5580
gatttctacg ggtgagttgg tggccgtgtc cacgcattgc atgagcccgt agctgcgcgg   5640
ggccacgacc gtgccgcggt gcgcttttag aagcggtgtc gcggacgcgc tcccggcggc   5700
agcggcggtt ccggccccgc gggcaggggc ggcagaggca cgtcggcgtg gcgctcgggc   5760
```

```
aggtcccggt gctgcgccct gagagcgctg gcgtgcgcga cgacgcgtcg gttgacatcc   5820
tggatctgcc gcctctgcgt gaagaccact ggccccgtga ctttgaacct gaaagacagt   5880
tcaacagaat caatctcggc gtcattgacg gcggcctgac gcaggatctc ttgcacgtcg   5940
cccgagttgt cctggtaggc gatttcggac atgaactgct cgatctcctc ctcctggaga   6000
tcgccgcggc cagcgcgctc gacggtggcg gcgaggtcat tcgagatgcg acccatgagc   6060
tgcgagaagg cgcccaggcc gctctcgttc cagacgcggc tgtagaccac gtccccgtcg   6120
gcgtcgcgcg cgcgcatgac cacctgcgcg aggttgagct ccacgtgccg cgtgaagacg   6180
gcgtagttgc gcaggcgctg gaagaggtag ttgagggtgg tggcgatgtg ctcggtgacg   6240
aagaagtaca tgatccagcg gcgcaggggc atctcgctga tgtcgccgat ggcctccagc   6300
ctttccatgg cctcgtagaa atccacggcg aagttgaaaa actgggcgtt gcgggccgag   6360
accgtgagct cgtcttccaa gagccggatg agctcggcga tggtggcgcg cacctcgcgc   6420
tcgaaacccc cgggggcctc ctcctcttcc tcttcttcca tgacgacctc ttcttctatt   6480
tcttcctctg gggggcggtgg tggtggcggg gcccgacgac gacggcggcg caccgggaga   6540
cggtcgacga agcgctcgat catctccccg cggcggcgac gcatggtttc ggtgacggcg   6600
cgaccccgtt cgcgaggacg cagcgtgaag acgccgccgg tcatctcccg gtaatggggc   6660
gggtccccgt tgggcagcga gagggcgctg acgatgcatc ttatcaattg cggtgtaggg   6720
gacgtgagcg cgtcgagatc gaccggatcg gagaatcttt cgaggaaagc gtctagccaa   6780
tcgcagtcgc aaggtaagct caaacacgta gcagccctgt ggacgctgtt agaattgcgg   6840
ttgctgatga tgtaattgaa gtaggcgttt ttaaggcggc ggatggtggc gaggaggacc   6900
aggtccttgg gtcccgcttg ctggatgcgg agccgctcgg ccatgcccca ggcctggccc   6960
tgacaccggc tcaggttctt gtagtagtca tgcatgagcc tttcaatgtc atcactggcg   7020
gaggcggagt cttccatgcg ggtgaccccg acgcccctga gcggctgcac gagcgccagg   7080
tcggcgacga cgcgctcggc gaggatggcc tgttgcacgc gggtgagggt gtcctggaag   7140
tcgtccatgt cgacgaagcg gtggtaggcc cctgtgttga tggtgtaggt gcagttggcc   7200
atgagcgacc agttgacggt ctgcaggccg ggttgcacga cctcggagta cctgatccgc   7260
gagaaggcgc gcgagtcgaa gacgtagtcg ttgcaggtgc gcacgaggta ctggtagccg   7320
actaggaagt gcggcggcgg ctggcggtag agtggccagc gctgggtggc cggcgctccc   7380
ggggccaggt cctcgagcat gaggcggtgg tagccgtaga ggtagcggga catccaggtg   7440
atgccggcgg cagtggtgga ggcgcgcggg aactcgcgga cgcggttcca gatgttgcgc   7500
agcggcagga aatagtccat ggtcggcacg gtctggccgg tgagacgcgc gcagtcattg   7560
acgctctaga ggcaaaaacg aaagcggttg agcgggctct tcctccgtag cctggcggaa   7620
cgcaaacggg ttaggccgcg tgtgtacccc ggttcgagtc ccctcgaatc aggctggagc   7680
cgcgactaac gtggtattgg cactcccgtc tcgacccgag cccgatagcc gccaggatac   7740
ggcggagagc ccttttttgcc ggccgagggg agtcgctaga cttgaaagcg gccgaaaacc   7800
ctgccgggta gtggctcgcg cccgtagtct ggagaagcat cgccagggtt gagtcgcggc   7860
agaacccggt tcgcggacgg ccgcggcgag cgggacttgg tcaccccgcc gatttaaaga   7920
cccacagcca gccgacttct ccagttacgg gagcgagccc cctttttttct tttgccaga   7980
tgcatcccgt cctgcgccaa atgcgtccca cccccccggc gaccaccgcg accgcggccg   8040
tagcaggcgc cggcgctgta gccccgccac agacagagat ggacttggaa gagggcgaag   8100
ggctggcgag actgggggcg ccgtccccgg agcgacaccc ccgcgtgcag ctgcagaagg   8160
```

```
acgtgcgccc ggcgtacgtg cctccgcaga acctgttcag ggaccgcagc ggggaggagc   8220
ccgaggagat gcgcgactgc cggtttcggg cgggcaggga gctgcgcgag ggcctggacc   8280
gccagcgcgt gctgcgcgac gaggatttcg agccgaacga gcagacgggg atcagccccg   8340
cgcgcgcgca cgtggcggcg gccaacctgg tgacggccta cgagcagacg gtgaagcagg   8400
agcgcaactt ccaaaagagt ttcaacaacc acgtgcgcac cctgatcgcg cgcgaggagg   8460
tggccctggg cttgatgcac ctgtgggacc tggcggaggc catcgtgcag aacccggaca   8520
gcaagcctct gacggcgcag ctgttcctgg tggtgcagca cagcagggac aacgaggcgt   8580
tcagggaggc gctgctgaac atcgccgagc ccgagggtcg ctggctgctg gagctgatta   8640
acatcttgca gagcatcgta gtgcaggagc gcagcttgag cctggccgag aaggtggcgg   8700
cgatcaacta ctcggtgctg agcctgggca agttttacgc gcgcaagatt tacaagacgc   8760
cgtatgtgcc catagacaag gaggtgaaga tagacagctt ttacatgcgc atggcgctca   8820
aggtgctgac gctgagcgac gacctgggcg tgtaccgcaa cgaccgcatc cacaaggccg   8880
tgagcacgag ccggcggcgc gagctgagcg accgcgagct gatgctgagc ctgcgccggg   8940
cgctggtagg gggcgccgcc ggcggcgagg agtcctactt cgacatgggg gcggacctgc   9000
attggcagcc gagccggcgc gccttggagg ccgcctacgg tccagaggac ttggaagagg   9060
atgaggaaga ggaggaggat gcacccgctg cggggtactg acgcctccgt gatgtgtttt   9120
tagatgtccc agcaagcccc ggaccccgcc ataagggcgg cgctgcaaag ccagccgtcc   9180
ggtctagcat cggacgactg ggaggccgcg atgcaacgca tcatggccct gacgacccgc   9240
aaccccgagt cctttagaca acagccgcag gccaacagac tctcggccat tctggaggcg   9300
gtggtcccct ctcggaccaa ccccacgcac gagaaggtgc tggcgatcgt gaacgcgctg   9360
gcggagaaca aggccatccg tcccgacgag gccgggctgg tgtacaacgc cctgctggag   9420
cgcgtgggcc gctacaacag cacgaacgtg cagtccaacc tggaccggct ggtgacggac   9480
gtgcgcgagg ccgtggcgca gcgcgagcgg ttcaagaacg agggcctggg ctcgctggtg   9540
gcgctgaacg ccttcctggc gacgcagccg gcgaacgtgc cgcgcgggca ggacgattac   9600
accaacttta tcagcgcgct gcggctgatg gtgaccgagg tgccccagag cgaggtgtac   9660
cagtcgggcc ctgactactt tttccagacg agccggcagg gcttgcagac ggtgaacctg   9720
agtcaggctt tcaagaacct gcgcgggctg tggggcgtgc aggcgcccgt gggcgaccgg   9780
tcgacggtga gcagcttgct gacgcccaac tcgcggctgc tgctgttgct gatcgcgccc   9840
tttactgaca gcggcagcgt aaaccgcaac tcgtacctgg gccacctgct gacgctgtac   9900
cgcgaggcca taggccaggc acaggtggac gagcagacct tccaggaaat tacgagcgtg   9960
agccgcgcgc tggggcagaa cgacaccgac agtctgaggg ccaccctgaa ctttttgctg  10020
accaatagac agcagaagat cccggcgcag tacgcactgt cggccgagga ggaaaggatc  10080
ctgagatatg tgcagcagag cgtagggctg ttcctgatgc aggagggtgc cacccccagc  10140
gccgcgctgg acatgaccgc gcgcaacatg gaacctagca tgtacgccgc caaccggccg  10200
ttcatcaata agctgatgga ctacctgcac cgcgcggcgg ccatgaacac ggactacttt  10260
accaacgcca tcctgaaccc gcactggctc ccgccgccgg gtttctacac gggcgagtac  10320
gacatgcccg accccaacga cgggttcctg tgggacgacg tggacagcgc ggtgttctcg  10380
ccggcctttc aaaagcgtca ggaggcgccg ccgagcgagg gcgcggtggg gagaagcccc  10440
tttcctagct tagggagttt gcatagcttg ccgggctcgg tgaacagcgg cagggtgagc  10500
```

cggccgcgct tgctgggcga ggacgagtac ctgaacgact cgctactgca gccgccgcgg 10560
gccaagaacg ccatggccaa taacgggata gagagtctgg tggacaaact gaaccgctgg 10620
aagacctacg ctcaggacca tagggacgcg cccgcgccgc ggcgacagcg ccacgaccgg 10680
cagcggggcc tggtgtggga cgacgaggac tcggccgacg atagcagcgt gttggacttg 10740
ggcgggagcg gtggggccaa cccgttcgca catctgcagc ccaaactggg gcggcggatg 10800
ttttgaaatg caaaataaaa ctcaccaagg ccatagcgtg cgttctcttc cttgttagag 10860
atgaggcgcg cggtggtgtc ttcctctcct cctccctcgt acgagagcgt gatggcgcag 10920
gcgaccctgg aggttccgtt tgtgcctccg cggtatatgg ctcctacgga gggcagaaac 10980
agcattcgtt actcggagct ggctccgcag tacgacacca ctcgcgtgta cttggtggac 11040
aacaagtcgg cggacatcgc ttctctgaac taccaaaacg accacagcaa cttcctgacc 11100
acggtggtgc agaacaacga tttcaccccc gccgaggcca gcacgcagac gataaatttt 11160
gacgagcggt cgcggtgggg cggtgatctg aagaccattc tgcacaccaa catgcccaat 11220
gtgaacgagt acatgttcac cagcaagttt aaggcgcggg tgatggtggc tagaaagcat 11280
cccaaagatg tagatgccag tgatttaagc aaggatatct tagagtatga ttggtttgag 11340
tttaccctgc ccgagggcaa cttttccgag accatgacca tagacctgat gaacaacgcc 11400
atcttggaaa actacttgca agtggggcgg caaaatggcg tgctggagag cgatatcggt 11460
gtcaagtttg acagcaggaa tttcaagctg ggctgggacc cggtgaccaa gctggtgatg 11520
cctggggtct acacctacga ggccttccac ccggacgtgg tgctgctgcc gggctgcggg 11580
gtggacttca ccgagagtcg tctgagcaac ctcctgggca ttcgcaagaa gcaacctttc 11640
caagagggct tcagaatcat gtatgaggat ctagtagggg gcaacatccc cgccctcctg 11700
aatgtcaagg agtatctgaa ggataaggaa gaagctggca cagcagatgc aaataccatt 11760
aaggctcaga atgatgcagt cccaagagga gataactatg catcagcggc agaagccaaa 11820
gcagcaggaa aagaaattga gttgaaggcc attttgaaag atgattcaaa cagaagctac 11880
aatgtgatcg agggaaccac agacaccctg taccgcagtt ggtacctgtc ctatacctac 11940
ggtgatcccg agaagggagt gcagtcgtgg acactgctta ccaccccgga cgtcacctgc 12000
ggcgcggagc aagtctactg gtcgctgccg gacctcatgc aagaccccgt caccttccgc 12060
tctacccagc aagtcagcaa ctaccccgtg gtcggcgccg agctcatgcc tttccgcgcc 12120
aagagctttt acaacgacct cgccgtctac tctcagctca tccgcagcta cacctccctc 12180
acccacgtct tcaaccgctt ccccgacaac cagatcctct gccgcccgcc cgcgcccacc 12240
atcaccaccg tcagtgaaaa cgtgcctgct ctcacagatc acgggacgct accgctgcgc 12300
agcagtatcc gcggagtcca gcgagtgacc gtcactgacg cccgtcgccg cacctgtccc 12360
tacgtctaca aggccctggg catagtcgcg ccgcgcgtgc tttccagtcg caccttctaa 12420
aaaatgtcta ttctcatctc gcccagcaat aacaccggct ggggtcttac taggcccagc 12480
accatgtacg gaggagccaa gaagcgctcc cagcagcacc ccgtccgcgt ccgcggccac 12540
ttccgcgctc cctggggcgc ttacaagcgc gggcggactt ccaccgccgc cgtgcgcacc 12600
accgtcgacg acgtcatcga ctcggtggtc gccgacgcgc gcaactatac ccccgccccc 12660
tccaccgtgg acgcggtcat cgacagcgtg gtggccgatg cacgcgacta tgccagacgc 12720
aagagccggc ggcgacggat cgccaggcgc caccggagca cgcccgccat gcgcgccgcc 12780
cgggctctgc tgcgccgcgc cagacgcacg ggccgccggg ccatgatgcg agccgcgcgc 12840
cgcgctgcca ctgcacccac ccccgcaggc aggactcgca gacgagcggc cgccgccgcc 12900

```
gccgcggcca tttctagcat gaccagaccc aggcgcggaa acgtgtactg ggtgcgcgac  12960
tccgtcacgg gcgtgcgcgt gcccgtgcgc acccgtcctc ctcgtccctg atctaatgct  13020
tgtgtcctcc cccgcaagcg acgatgtcaa agcgcaaaat caaggaggag atgctccagg  13080
tcgtcgcccc ggagatttac ggacccccgg accagaaacc ccgcaaaatc aagcgggtta  13140
aaaaaaagga tgaggtggac gagggggcag tagagtttgt gcgcgagttc gctccgcggc  13200
ggcgcgtaaa ttggaagggg cgcagggtgc agcgcgtgtt gcggcccggc acggcggtgg  13260
tgttcacgcc cggcgagcgg tcctcggtca ggagcaagcg tagctatgac gaggtgtacg  13320
gcgacgacga catcctggac caggcggcgg agcgggcggg cgagttcgcc tacgggaagc  13380
ggtcgcgcga agaggagctg atctcgctgc cgctggacga aagcaacccc acgccgagcc  13440
tgaagcccgt gaccctgcag caggtgctgc cccaggcgat gctgctgccg agccgcgggg  13500
tcaagcgcga gggcgagagc atgtacccga ccatgcagat catggtgccc aagcgccggc  13560
gcgtggagga cgtgctggac accgtgaaaa tggatgtgga gcccgaggtc aaggtgcgcc  13620
ccatcaagca ggtggcgccg ggcctgggcg tgcagaccgt ggacattcag atccccaccg  13680
acatggatgt cgacaaaaaa ccctcgacca gcatcgaggt gcagactgac ccctggctcc  13740
cagcctccac cgctaccgtc tctacttcta ccgccgccac ggctaccgag cctacaagga  13800
ggcgaagatg ggcgccgcc agccggctga tgcccaacta cgtgttgcat ccttccatca  13860
tcccgacgcc gggctaccgc ggcacccggt actacgccag ccgcaggcgc ccagccagca  13920
aacgccgccg ccgcaccgcc acccgccgcc gtctggcccc cgcccgcgtg cgccgcgtaa  13980
ccacgcgccg gggccgctcg ctcgttctgc ccaccgtgcg ctaccacccc agcatccttt  14040
aatccgtgtg ctgtgatact gttgcagaga gatggctctc acttgccgcc tgcgcatccc  14100
cgtcccgaat taccgaggaa gatcccgccg caggagaggc atggcaggca gcggcctgaa  14160
ccgccgccgg cggcgggcca tgcgcaggcg cctgagtggc ggctttctgc ccgcgctcat  14220
ccccataatc gccgcggcca ttggcacgat cccgggcata gcttccgttg cgctgcaggc  14280
gtcgcagcgc cgttgatgtg cgaataaagc ctctttagac tctgacacac ctggtcctgt  14340
atatttttag aatggaagac atcaattttg cgtccctggc tccgcggcac ggcacgcggc  14400
cgttcatggg cacctggaac gagatcggca ccagccagct gaacgggggc gccttcaatt  14460
ggagcagtgt ctggagcggg cttaaaaatt tcggctcgac gctccggacc tatgggaaca  14520
aggcctggaa tagtagcacg gggcagttgt taagggaaaa gctcaaagac cagaacttcc  14580
agcaaaaggt ggtggacggc ctggcctcgg gcattaacgg ggtggtggac atcgcgaacc  14640
aggccgtgca gcgcgagata aacagccgcc tggacccgcg gccgcccacg gtggtggaga  14700
tggaagatgc aactcttccg ccgcccaaag gcgagaagcg cccgcggccc gacgcggagg  14760
agacgatcct gcaggtggac gagccgccct cgtacgagga ggccgtcaag gccggcatgc  14820
ccaccacgcg catcatcgcg ccgctggcca cgggtgtaat gaaacccgcc acccttgacc  14880
tgcctccacc acccacgccc gctccaccga aggcagctcc ggtcgtgcag gccccccccgg  14940
tggcgaccgc cgtgcgccgc gtccccgccc gccgccaggc ccagaactgg cagagcacgc  15000
tgcacagtat cgtgggcctg ggagtgaaaa gtctgaagcg ccgccgatgc tattgagaga  15060
gaggaaagag gacactaaag ggagagctta acttgtatgt gccttaccgc cagagaacgc  15120
gcgaagatgg ccaccccctc gatgatgccg cagtgggcgt acatgcacat cgccgggcag  15180
gacgcctcgg agtacctgag cccgggtctg gtgcagtttg cccgcgccac cgacacgtac  15240
```

```
ttcagcctgg gcaacaagtt taggaacccc acggtggctc ccacccacga tgtgaccacg 15300
gaccggtccc agcgtctgac gctgcgcttc gtgcccgtgg atcgcgagga caccacgtac 15360
tcgtacaagg cgcgcttcac tctggccgtg ggagacaacc gggtgctaga catggccagc 15420
acttactttg acatccgcgg cgtcctggac cgcggtccca gcttcaaacc ctactcgggc 15480
acggcttaca acagcctggc ccccaagagc gctcccaatc ccagccagtg ggatgcaaag 15540
gaaaaggaag gagttgccca aacagaaaaa aatgttttaa aaacatttgg tgttgccgct 15600
acaggtggtt ttaatattac agatcagggt ttgttacttg gaactgagga aacagctgaa 15660
aacgttaaaa aggatatcta tgcagagaaa actttccagc ctgaacctca agttggtgaa 15720
gaaaactggc aggaaagtga agccttttat ggaggaaggg ctattaagaa agacaccaaa 15780
atgaagccat gctatggttc atttgccaga cccactaatg aaaaaggagg acaggctaaa 15840
tttaaaacac tagatgggca agttacaaaa gatccagata ttgactttgc ttactttgac 15900
gtccctggcg gaaaagctcc aacaggcagt agtctaccgg aagaatacaa agcagatata 15960
attttgtaca cagaaaatgt taatctggaa acaccagata ctcacatagt gtataaacct 16020
ggcaaagaag atgacaattc tgaaattaac ttaacacaac agtccatgcc aaacagaccc 16080
aactacattg gctttaggga caactttgta ggtctcatgt actacaacag tactggcaac 16140
atgggtgtgc tggctggtca ggcctctcag ttgaatgctg tggtggactt gcaagacaga 16200
aacaccgagc tgtcttacca gctcttgcta gattctctgg gtgacagaac cagatacttt 16260
agcatgtgga actctgcggt tgacagttat gatcccgatg tcaggatcat tgagaatcac 16320
ggtgtggaag atgaacttcc aaactattgc ttcccattga atggcactgg taccaattcc 16380
acctatcaag gtgtaaaaat tacaggtaat aatgatggcg atcttgaaac cgaatgggaa 16440
agagatgaag caatctctag acaaaaccaa atctgcaagg gcaacgtcta tgccatggag 16500
atcaacctcc aggccaacct gtggaagagt tttctgtact cgaacgtagc cctgtacctg 16560
cctgactcat acaagtacac gccggccaac gtcacgctgc ccgccaacac caacacctac 16620
gagtacatga acggccgcgt ggtagccccc tcgctggtgg acgcttacat caacatcggc 16680
gcccgctggt cgctggatcc catggacaat gtaaacccat tcaaccacca ccgcaacgcg 16740
ggcctgcgct accgttccat gttgttgggc aacggtcgct acgtgccctt ccacatccaa 16800
gtgccccaaa agttctttgc catcaagaac ctgcttctgc tcccgggctc ctacacctac 16860
gagtggaact tccgcaagga cgtcaacatg atcctgcaga gttccctcgg aaacgatctg 16920
cgcgtcgacg gcgcctccgt ccgcttcgac agcgtcaacc tctacgccac cttcttcccc 16980
atggcgcaca acaccgcctc caccctggaa gccatgctgc gcaacgacac caacgaccag 17040
tccttcaacg actacctctc ggccgccaac atgctctacc ccatcccggc caaggccacc 17100
aacgtgccca tctccatccc ctcacgcaac tgggccgcct tccgcggctg gagtttcacc 17160
aggctcaaga ccaaggaaac tccctcgcta ggctcgggtt tcgacccata ctttgtctac 17220
tcgggctcca tcccctatct cgacgggacc ttctacctca atcacacctt caagaaggtc 17280
tccatcatgt tcgactcctc ggtcagctgg cccggcaacg accggctgct cacgccgaac 17340
gagttcgaga tcaagcgcag cgtcgacggg gagggctaca acgtggccca atgcaacatg 17400
accaaggact ggttcctcgt ccagatgctc tcccactaca acatcggcta ccagggcttc 17460
cacgtgcccg agggctacaa ggaccgcatg tactccttct tccgcaactt ccagcccatg 17520
agcaggcagg tggtcgatga gatcaactac aaggactaca aggccgtcac cctgcccttc 17580
cagcacaaca actcgggctt caccggctac ctcgcaccca ccatgcgtca ggggcagccc 17640
```

```
taccccgcca acttccccta cccgctcatc ggccagacag ccgtgccctc cgtcacccag  17700
aaaaagttcc tctgcgacag ggtcatgtgg cgcatcccct tctccagcaa cttcatgtcc  17760
atgggcgccc tcaccgacct gggtcagaac atgctctacg ccaactcggc ccatgcgctc  17820
gacatgacct tcgaggtgga ccccatggat gagcccaccc tcctctatct tctcttcgaa  17880
gttttcgacg tggtcagagt gcaccagccg caccgcggcg tcatcgaggc cgtctacctg  17940
cgcacgccct tctccgccgg aaacgccacc acataagcat gagcggctcc agcgaaagag  18000
agctcgcggc catcgtgcgc gacctgggct gcgggcccta ctttttgggc acccacgaca  18060
agcgcttccc tggcttcctc gccggcgaca agctggcctg cgccatcgtc aacacggccg  18120
gccgcgagac cggaggcgtg cactggctcg ccttcggctg gaacccgcgc tcgcgcacct  18180
gctacatgtt cgacccattt gggttctcgg accgccggct caagcagatt tacagcttcg  18240
agtacgaggc tatgctgcgc cgaagcgccc tggcttcctc gccagaccgc tgtctcagcc  18300
tcgagcagtc cacccagacc gtgcaggggc ccgactccgc cgcctgcgga cttttctgtt  18360
gcatgttctt gcatgccttc gtgcactggc ccgaccgacc catggacggg aaccccacca  18420
tgaacttgct gacgggggtg cccaacggca tgctacaatc gccacaggtg ctgcccaccc  18480
tccggcgcaa ccaggaggag ctctaccgct tcctcgcgcg ccactcccct tactttcgat  18540
cccaccgcgc cgccatcgaa cacgccaccg cttttgacaa aatgaaacaa ctgcgtgtat  18600
ctcaataaac agcactttta ttttacatgc actggagtat atgcaagtta tttaaaagtc  18660
gaaggggttc tcgcgctcgt cgttgtgcgc cgcgctgggg agggccacgt tgcggtactg  18720
atacttgggc tgccacttga actcggggat caccagtttg ggcactgggg tctcggggaa  18780
ggtctcgctc cacatgcgcc ggctcatctg cagggcgccc agtatgtccg ggcggagat  18840
cttgaaatcg cagttggggc cggtgctctg cgcgcgcgag ttgcggtaca cggggttgca  18900
gcactggaac accatcagac tggggtactt cacactggcc agcacgctct tgtcgctgat  18960
ctgatccttg tccaggtcct cggcgttgct caggccgaac ggggtcatct tgcacagctg  19020
gcggcccagg aagggcacgc tctgaggctt gtggttacac tcgcagtgca cgggcatcag  19080
catcatcccc gcaccgcgct gcatattcgg gtagagggcc ttgacaaagg ccgagatctg  19140
cttgaaagct tgctgggcct tggccccctc gctgaagaac agaccacagc tcttcccgct  19200
gaactggtta ttcccgcacc cggcatcatg cacgcagcag cgcgcgtcat ggctggtcag  19260
ttgcaccacg ctccgtcccc agcggttctg ggtcaccttg gccttgctgg gttgctcctt  19320
caacgcgcgc tgcccgttct cgctggtcac atccatctcc accacgtggt ccttgtggat  19380
catcaccgtc ccatgcagac acttgagctg gccttccacc tcggtgcagc cgtgatccca  19440
cagggcgcat ccggtgcact cccaattctt gtgtgcgatc ccgctgtggc tgaagatgta  19500
accttgcaac atgcggccca tgacggtgct aaatgctttc tgggtggtga aggtcagttg  19560
catcccgcgg acctcctcgt tcatccaggt ctggcacatc ttctggaaga tctcggtctg  19620
ctcgggcatg agcttgtaag catcgcgcag gccgctgtcg acgcggtagc gttccatcag  19680
tacgttcatg gtatccatgc ccttctccca ggacgagacc agaggcagac tcagggggtt  19740
gcgcacgttc aggacacctg gggtcgcggg ctcgacgatg cgttttccgt ccttgtcttc  19800
cttcaacaga accggaggct ggctgaatcc cactcccacg atcacggcat cttcctgggg  19860
catctcttcg tcggggtcta ccttggtcac atgcttggtc tttctggctt gcttcttttt  19920
tggaggactg tccacgggga ccacgtcctc ctcggaagac ccggagccca cccgctgata  19980
```

```
ctttcggcgc ttggtgggca gaggaggtgg cggcgagggg ctcctctcct gctccggcgg  20040
atagcgcgcc gacccgtggc cccggggcgg agtggcctct cggtccatga accggcgcac  20100
gtcctgactg ccgccggcca ttatttccta ggggaagatg gaggagcagc cgcgtaagca  20160
ggagcaggag gaggacttaa ccacccacga gcaacccaaa atcgagcagg acctgggctt  20220
cgaagagccg gctcgtctag aaccccccaca ggatgaacag gagcacgagc aagacgcagg  20280
ccaggaggag accgacgctg ggctcgagca tggctacctg ggaggagagg aggatgtgct  20340
gctgaaacac ctgcagcgcc agtccctcat cctccgggat gccctggccg accggagcga  20400
aacccccctc agcgtcgagg agctgtgtcg ggcctacgag ctcaacctat tctcgccgcg  20460
cgtgcccccc aaacgccagc ccaacggcac atgcgagccc aacccgcgtc tcaacttcta  20520
tcccgtcttt gcggtccccg aggcccttgc cacctatcac atctttttca agaaccaaaa  20580
gatccccgtc tcctgtcgcg ccaaccgcac ccgcgccgac gcgctcctcg ctctggggcc  20640
cggcgcacac atacctgata tcgcttccct ggaagaggtg cccaagatct tcgaagggct  20700
cggtcgggac gagacgcgcg cggcgaacgc tctgaaagaa acagcagagg aagagggtca  20760
cactagcgcc ctggtagagt tggaaggcga caacgctagg ctggccgtgc tcaagcgcag  20820
tgtcgagctc acccacttcg cctaccccgc cgtcaacctc ccgcccaagg tcatgcgtcg  20880
catcatggat cagctcatca tgccccacat cgaggccctc gatgaaagtc aggagcagcg  20940
ccccgaggac gtccggcccg tggtcagcga cgagatgctc gcgcgctggc tcggaacccg  21000
cgacccccag gctttggaac agcggcgcaa actcatgctg gccgtggtcc tggtcaccct  21060
cgagctcgaa tgcatgcgcc gcttcttcag cgaccccgag accctacgca aagtcgagga  21120
aaccctgcac tacactttca gacacggctt cgtcaggcag gcctgcaaga tctccaacgt  21180
ggagctgacc aacctggtct cctgcctggg tatccttcac gagaaccgcc tggggcagac  21240
cgtgctccac tctaccctga agggcgaggc gcgtcgggac tatgtccgcg actgcatctt  21300
tctctttctc tgccacacat ggcaagcggc catgggcgtg tggcagcagt gtctcgagga  21360
cgagaacctg aaggagctgg acaaggttct tgctagaaac cttaaaaagc tgtggacggg  21420
cttcgacgag cgcaccgtcg cctcggacct ggcccagatc gtcttccccg agcgcctgag  21480
gcagacgctg aaaggcgggc tgccagactt catgagccag agcatgatac aaaactaccg  21540
cactttcatt ctcgagcgat ctggaatgct gcccgccacc tgcaacgcct tcccctccga  21600
ctttgtcccg ctgagctacc gcgagtgtcc cccgccgctg tggagccatt gctacctctt  21660
gcagctggcc aactacatcg cctaccactc ggacgtgatc gaggacgtga gcggcgaggg  21720
gcttctcgag tgccactgcc gctgcaacct gtgctccccg caccgctccc tggtctgcaa  21780
cccccagctc ctgagcgaga cccaggtcat cggtaccttc gagctgcaag gtccgcagga  21840
gtccaccgct ccgctgaaac tcacgccggg gttgtggact tccgcgtacc tgcgcaaatt  21900
tgtacccgag gactaccacg cccatgagat aaagttcttc gaggaccaat cgcgtccgca  21960
gcacgcggat ctcacggcct gcgtcatcac ccagggcgcg atcctcgccc aattgcacgc  22020
catccaaaaa tcccgccaag agtttcttct gaaaaagggt agaggggtct acctggaccc  22080
ccagacgggc gaggtgctca acccgggtct cccccagcat gccgaggaag aagcaggagc  22140
cgctagtgga ggagatggaa gaagaatggg acagccaggc agaggaggac gaatgggagg  22200
aggagacaga ggaggaagaa ttggaagagg tggaagagga gcaggcaaca gagcagcccg  22260
tcgccgcacc atccgcgccg gcagccccgg cggtcacgga tacaacctcc gcagctccgg  22320
ccaagcctcc tcgtagatgg gatcgagtga agggtgacgg taagcacgag cggcagggct  22380
```

```
accgatcatg gagggcccac aaagccgcga tcatcgcctg cttgcaagac tgcgggggga  22440
acatcgcttt cgcccgccgc tacctgctct tccaccgcgg ggtgaacatc ccccgcaacg  22500
tgttgcatta ctaccgtcac cttcacagct aagaaaaaat cagaagtaag aggagtcgcc  22560
ggaggaggcc tgaggatcgc ggcgaacgag cccttgacca ccagggagct gaggaaccgg  22620
atcttcccca ctctttatgc catttttcag cagagtcgag gtcagcagca agagctcaaa  22680
gtaaaaaacc ggtctctgcg ctcgctcacc cgcagttgct tgtaccacaa aaacgaagat  22740
cagctgcagc gcactctcga agacgccgag gctctgttcc acaagtactg cgcgctcact  22800
cttaaagact aaggcgcgcc cacccggaaa aaaggcggga attacctcat cgccaccatg  22860
agcaaggaga ttcccacccc ttacatgtgg agctatcagc cccagatggg cctggccgcg  22920
ggcgcctccc aagactactc cacacgcatg aactggctca gtgccggccc ctcgatgatc  22980
tcacgggtca acggggtccg cagtcatcga aaccagatat tgttggagca ggcggcggtc  23040
acctccacgc ccagggcaaa gctcaacccg cgtaattggc cctccaccct ggtgtatcag  23100
gaaatccccg ggccgactac cgtactactt ccgcgtgacg cactggccga agtccgcatg  23160
actaactcag gtgtccagct ggccggcggc gcttcccggt gcccgctccg cccacaatcg  23220
ggtataaaaa ccctggtgat ccgaggcaga ggcacacagc tcaacgacga gttggtgagc  23280
tcttcgatcg gtctgcgacc ggacggagtg ttccaactag ccggagccgg gagatcctcc  23340
ttcactccca accaggccta cctgaccttg cagagcagct cttcggagcc tcgctccgga  23400
ggcatcggaa ccctccagtt cgtggaggag tttgtgccct cggtctactt caacccccttc  23460
tcgggatcgc caggcctcta cccggacgag ttcataccga acttcgacgc agtgagagaa  23520
gcggtggacg gctacgactg aatgtcccat ggtgactcgg ctgagctcgc tcggttgagg  23580
catctggacc actgccgccg cctgcgctgc ttcgcccggg agagctgcgg actcatctac  23640
tttgagtttc ccgaggagca ccccaacggc cctgcacacg gagtgcgaat caacgtagag  23700
ggcaccaccg agtctcacct ggtcaggttc ttcacccagc aacccttcct ggtcgagcgg  23760
gaccggggcg ccaccaccta caccgtctac tgcatctgtc ctaacccgaa gttgcatgag  23820
aatttttgct gtactctttg tggtgagttt aataaaagct gaactaagaa cctactttgg  23880
aatcccttgt cgtcatcctc gaaacaagac cgtcttcttt accaaccaga ccaaggttcg  23940
tctgaactgc acaaccaaca ggaagtacct tctctggact ttccaaaaca cctcactcgc  24000
tgttgtcaat acccgtgacg acgtcaaccc catagtcatc acccagcagt cgggcgagac  24060
caacggctgc atccactgct cctgcgaaag ccccgagtgc atctactccc tcctcaagac  24120
cctttgcgga ctccgcgacc tcctccccat gaactgatgt tgattaaaag cccaaaaacc  24180
aatcataccc ttcccccatt tccccatccc caattactca taagaataaa tcattggaac  24240
taatcattca ataaagatca cttacttgaa atctgaaagt atgtctctgg tgtagttgtt  24300
cagcagcacc tcggtaccct cctcccagct ctggtactcc agtccccggc gggcggcgaa  24360
cttcctccac accttgaaag ggatgtcaaa ttcctggtcc acaattttca ttgtcttccc  24420
tctcagatga caaagaggct ccgggtggaa gatgacttca accccgtcta cccctatggc  24480
tacgcgcgga atcagaatat ccccttcctc actccccccct ttgtttcttc cgatggattc  24540
caaaacttcc cacccggggt attgtcactc aaactggctg acccaatagc catcgtcaat  24600
ggggatgtct cactcaaggt gggaggtgga ctcactttgc aagaaggaaa cctaactgtt  24660
gatgcaaagg ctccattgca agttgcaaat gacaacaaat tggagctttc ttatgcagac  24720
```

```
ccatttgagg ttaaagacac taagctacaa ttaaaagtag gtcatggttt aaaagtaata  24780
gatgaaaaaa cttcttcagg tcttcaaagt ctaattggaa atctcgtagt tttaacagga  24840
aaaggaattg gcactcaaga attaaaagac aaagacgatg aaactaaaaa tataggagtt  24900
ggaataaatg tgagaatagg gaaaaacgaa agtctggcgt ttgacaaaga tggaaatttg  24960
gtagcatggg ataatgaaaa cgacaggcgc actctatgga caactccaga cacatctcca  25020
aattgtaaaa taagtactga aaaagactcc aaacttactt tagtccttac taaatgcgga  25080
tctcaaattc tagcaagtgt gtctttgctt gctgtcgctg gaagttatct taatatgaca  25140
gctagtactc aaaagagtat aaaggtatct ttgatgtttg actcaaaagg gcttctaatg  25200
actacatctt ctattgataa aggatattgg aattatagaa ataaaaacag cgttgttgga  25260
actgcttatg aaaacgcaat tccatttatg ccaaatttag tggcttatcc aagacctaac  25320
acgccagact ctaaaattta tgctagaagc aaaattgttg gaaatgttta tttagcaggt  25380
ttggcttacc aaccaattgt cataacagtt agttttaatc aggagaagga tgcaagttgt  25440
gcttactcaa taacatttga atttgcctgg aacaaagact acgttggtca atttgatacc  25500
acctccttta ccttctctta tattgcccaa gaatgaaaga ccaataaacg tgtttttcat  25560
ttgaaaattt tcatgtatct ttattgattt ttacaccagc acgggtagtc agtctcccac  25620
caccagccca tttcacagtg taaacaattc tctcagcacg ggtggcctta aatagggaa  25680
tgttctgatt agtgcgggaa ctgaacttgg ggtctataat ccacacagtt tcctggcgag  25740
ccaaacgggg gtcggtgatt gagatgaagc cgtcctctga aaagtcatcc aagcgggcct  25800
cgcagtccaa ggtcacagtc tggtggaatg agaagaacgc acagattcat actcggaaaa  25860
caggatgggt ctgtgcctct ccatcagcgc cctcaacagt ctttgccgcc ggggctcggt  25920
gcggctgctg cagatgggat cgggatcgca agtctctctg actatgatcc ccacagcctt  25980
cagcatcagt ctcctggtgc gtcgggcaca gcaccgcatc ctgatctcgc tcatgttctc  26040
acagtaagtg cagcacataa tcaccatgtt attcagcagc ccataattca ggatgctcca  26100
gccaaagctc atgttgggga tgatggaacc cacgtgacca tcataccaga tgcggcagta  26160
tatcaggtgc ctgcccctca tgaacacact gcccatatac atgatctctt tgggcatgtt  26220
tctgttcaca atctgccggt accaggggaa tcgctggttg aacatgcacc cgtaaatgac  26280
tctcctgaac cacacggcca gcagggtgcc tcccgcccga cactgcaggg agcccgggga  26340
tgaacagtgg caatgcagga tccagcgctc gtacccgctc accatctgag ctctcaccaa  26400
gtccagggta gcaggacaca ggcacactga catacatctt tttaaaattt ttatttcctc  26460
tggggacagg atcatatccc aggggactgg aaactcttgg agcagggtaa agccagcagc  26520
acatggcaat ccacggacag aacttacatt atgataatct gcatgatcac aatcgggcaa  26580
cagagggtgt tgttcagtca gagaggccct ggtctcctca tcagatcgtg gtaaacgggc  26640
cctgcgatat ggatgatggc ggagcaagct cgactgatcc tcggtttgca ttgtagtgga  26700
ttctcttgcg taccttgtcg tacttctgcc agcagaaatg ggcccttgaa cagcagatac  26760
ctctccttct cctgtctttc cgctgctgac gctcagtcat ccaactgaag tacagccatt  26820
cccgcaggtt ctcgagcagc tcctcagcat ctgatgaaac aaaagttctg tccatgcgga  26880
ttccccttaa cacatcagcc aggacattgt aggccatccc aatccagtta atgcagcctg  26940
gtctatcatt cagaggaggt gggggaagaa ctggaagaac catttttatt ccaagcggtc  27000
tcgaaggatg ataaagtgca agtcacgcag gtgacagcgt tccccgccgc tgtgctggtg  27060
gaaacagaca gccaggtcaa aacctactct attttcaagg tgctcgactg tggcttcgag  27120
```

```
cagtggctct acgcgtacat ccagcataag aatcacatta aaggctggcc ctccatcgat  27180

ttcatcaatc atcaggttac actcattcac cattcccagg taattctcat ttttccagcc  27240

ttgaattatt tctacaaatt gttggtgtaa gtccactccg cacatgtgga aaagttccca  27300

cagcgccccc tccactttca taatcaggca gaccttcata atagcaacag atctggctgc  27360

tccaccacct gcagcgtgtt caaaacaaca agattcaatg agtttctgcc ctctgccctg  27420

agctcgcgtc tcagcgtcag ctgtaaaaag tcactcaagt cctcggccac tacagatgcc  27480

aattcagagc cagggctaag cgtgggactg gcaagcgtga tggagtactt taatgctcca  27540

aagctagcac ccaaaaactg cacgctggaa taagctctct ttgtgtcacc ggtgattcct  27600

tccaaaaggt gagtgataaa gcgaggtagg tgctctctaa tcatagcagt aatggaaaag  27660

tcctctaaat aagtcactag ggccccaggg accacaatgt ggtagctgac agcgcgtcgc  27720

tcaagcatgg ttagtagaga tgagagtctg aaaaacagaa agcatgcact aaaccagagt  27780

ggcaagtctt actgaaggaa aaatcactct ctccagcagc aaagtgccca ctgggtggcc  27840

ctctcggaca tacaaaaatc gatccgtgtg gttaaagagc agcacagtta gctactgtct  27900

tctcccagca aagatcacat cggactgggt tagtatgccc ctggaatggt agtcattcaa  27960

ggccataaat ctgccttggt agccattagg aatcagcacg ctcactctca agtgaaccaa  28020

aaccacccca tgcggaggaa tgtggaaaga ttcggggcaa aagaaattat atctattgct  28080

agtcccttcc tggacgggag cgattcctcc agggctatct atgaaagcat acagagattc  28140

agccatagct cagcccgctt accagtagac agagagcaca gcagtacaag cgccaacagc  28200

agcgactgac tacccactaa cccagctccc tatttaaagg caccttacac tgacgtaatg  28260

accaaaggtc taaaaacccc gccaaaaaaa aacacacacg ccctgggtgt ttttcgcgaa  28320

aacacttccg cgttctcact tcctcgtatc gatttcgtga ctcaacttcc gggttcccac  28380

gttacgtcac ttctgccctt acatgtaact cagccgtagg gtgccatctt gcccacgtcc  28440

aagatggctt ccatgtccgg ccacgcctcc gcggcgaccg tcagccgtgc gtcgtgacgt  28500

cactaacggt tcttgcaacg gccaatcagc gacggccccg ccctaaattc aaaagctcat  28560

ttgcatatta acttttgttt actttgtggg gtatattatt gatgatg                28607
```

<210> SEQ ID NO 11
<211> LENGTH: 2094
<212> TYPE: DNA
<213> ORGANISM: Herpes Simplex Virus

<400> SEQUENCE: 11

```
atgtctgtga gaggacacgc cgtgagaaga agaagagcca gcaccagatc tcatgcccca     60

tctgcccaca gagctgatag ccctgtggag gatgaacctg aaggcggcgg agtgggactg    120

atgggatacc tgcgggccgt gttcaacgtg gacgacgatt ctgaagtgga agccgctggc    180

gaaatggcct ctgaggaacc ccctcctcgg agaagaagag aggctagagg ccaccctgga    240

agcagaagag cctctgaagc cagagctgct gcccctccta gaagagctag cttccccaga    300

cctagaagcg tgacagccag atcccagagc gtgagaggca gaagagatag cgccatcacc    360

agagccccta gaggcggata tctgggcccc atggacccta gagatgtgct gggaagagtg    420

ggcggatcta gagtggtgcc tagccccctg tttctggacg agctgaacta cgaagaggac    480

gattatcctg ccgccgtggc ccatgatgat ggacctggcg ccagaccttc tgccacagtg    540

gagatcctgg ccggaagagt gtctggacct gaactgcagg ccgccttccc tctggataga    600
```

```
ctgacaccta gagtggccgc ctgggatgag tctgtgagat ctgccctggc tctgggacat    660
ccagccggct tttacccttg tcccgatagc gcctttggcc tgtctagagt gggcgtgatg    720
cactttgcta gccctgccga ccctaaggtg ttcttcaggc agacactgca gcagggcgaa    780
gctctggctt ggtacgtgac aggcgacgcc attctggatc tgaccgacag aagagccaag    840
accagccctt ctagagccat gggctttctg gtggacgcca ttgtgagagt ggccatcaat    900
ggatgggtgt gcggcacaag actgcacaca gagggcagag gctctgagct ggatgataga    960
gccgccgaac tgagaaggca gtttgcctct ctgacagccc tgagacctgt gggagctgct   1020
gctgtgcctc tgctgtctgc tggcggagct gctcctcctc atcctggacc tgatgccgcc   1080
gtgtttagaa gcagcctggg cagcctgctg tattggcctg gcgtgagagc cctgctgggc   1140
agagattgta gagtggctgc cagatacgca ggcaggatga cctatattgc cacaggcgcc   1200
ctgctggcta gattcaatcc tggcgccgtg aaatgtgtgc tgcctaggga agccgctttt   1260
gctggcagag tgctggatgt gctggccgtg ctggctgaac agacagtgca gtggctgtct   1320
gtggtggtgg gagctagact gcatcctcac tctgcccatc ctgcctttgc cgatgtggaa   1380
caggaagccc tgtttagagc cctgccactg ggatctccag gcgtggtggc cgctgaacat   1440
gaagctctgg gcgatacagc tgctagaagg ctgctggcca catctggact gaatgccgtg   1500
ctgggagccg ctgtgtatgc tctgcatacc gccctggcta cagtgacact gaagtacgcc   1560
ctggcctgtg gagatgctag aagaaggcgg gacgacgctg ctgctgctag ggctgtgctg   1620
gctacaggac tgatcctgca gagactgctg ggactggctg atacagtggt ggcttgtgtg   1680
gccctggctg cttttgatgg cggaagcaca gctcctgaag tgggcaccta cacccctctg   1740
agatacgcct gtgtgctgag agctacccag cctctgtacg ccagaacaac ccctgccaag   1800
ttctgggctg atgtgagagc cgctgccgaa catgtggatc tgagacctgc ctcttctgct   1860
cctagagccc ctgtgtctgg aactgccgat ccagccttcc tgctggaaga tctggccgct   1920
tttcctcctg cccctctgaa tagcgagtct gtgctgggcc ctagagtgag agtggtggac   1980
atcatggccc agttccggaa actgctgatg ggcgatgaag aaacagccgc cctgagagcc   2040
cacgtgtcag gaagaagagc tacaggcctg ggaggacctc ctagaccttg atga         2094
```

<210> SEQ ID NO 12
<211> LENGTH: 4125
<212> TYPE: DNA
<213> ORGANISM: Herpes Simplex Virus

<400> SEQUENCE: 12

```
atggctgccc ctgccagaga tccccctggc tacagatacg ccgctgccat cctgcctacc     60
ggcagcatcc tgagcaccat cgaggtggcc agccacagac ggctgttcga cttcttcgcc    120
gccgtgcgga gcgatgagaa cagcctgtac gacgtggagt tcgacgccct gctgggcagc    180
tactgcaaca ccctgagcct ggtccggttc ctggaactgg gcctgagcgt ggcctgtgtg    240
tgcaccaagt tccccgagct ggcctacatg aacgagggcc gggtgcagtt tgaggtgcac    300
cagcccctga tcgccagaga tggcccccac cctgtggagc agcccgtgca caactacatg    360
accaaggtga tcgacagacg ggccctgaat gccgccttta gcctggccac agaggccatc    420
gccctgctga caggcgaagc cctggatggc accggcatca gcctgcacag gcagctgagg    480
gccattcagc agctggcccg gaatgtgcag gctgtgctgg gcgcctttga gagaggcacc    540
gccgaccaga tgctgcacgt gctgctggaa aaggcccctc ctctggccct gctgctgccc    600
atgcagagat acctggacaa cggccggctg gccacaagag tggccagagc caccctggtg    660
```

```
gccgagctga agcggagctt ctgcgatacc agcttcttcc tgggcaaggc cggccacaga    720

agggaagcca tcgaggcctg gctggtcgat ctgaccaccg ccacccagcc atctgtggcc    780

gtgcccagac tgacccacgc cgacaccaga ggcagacccg tggatggcgt gctggtgacc    840

acagccgcca tcaagcagcg gctgctgcag agcttcctga aggtggagga caccgaggcc    900

gatgtgcctg tgacctacgg cgagatggtg ctgaacggcg ccaatctggt gaccgccctg    960

gtgatgggca aagccgtgag atccctggac gacgtgggca gacacctgct ggacatgcag   1020

gaagagcagc tggaagccaa ccgggagacc ctggatgagc tggaaagcgc ccctcagacc   1080

accagagtgc gggccgatct ggtggccatc ggcgacaggc tggtgttcct ggaagctctg   1140

gaacggcgga tctacgccgc caccaacgtg ccttaccctc tggtcggcgc catggacctg   1200

accttcgtgc tgcccctggg cctgttcaac cccgccatgg aaaggtttgc cgcccacgcc   1260

ggcgatctgg tgcctgcccc tggccaccct gaacccagag ccttcccccc cagacagctg   1320

ttcttctggg gcaaggacca ccaggtgctg agactgagca tggaaaacgc cgtgggcacc   1380

gtgtgtcacc ccagcctgat gaacatcgac gccgccgtgg gcggagtgaa ccacgatcct   1440

gtggaggccg ccaatcccta cggcgcctac gtggctgctc ctgctggacc aggcgccgac   1500

atgcagcagc ggtttctgaa cgcctggcgg cagagactgg cccacggcag agtgagatgg   1560

gtggccgagt gccagatgac cgccgagcag ttcatgcagc ccgacaacgc caacctggcc   1620

ctggaactgc accccgcctt cgatttcttt gccggcgtgg ccgatgtgga actgccaggc   1680

ggcgaagtgc ctccagctgg ccctggcgcc atccaggcca catggcgggt ggtgaacggc   1740

aatctgccac tggccctgtg ccctgtggcc ttcagagatg ccagggggct ggaactggga   1800

gtgggcaggc atgccatggc ccctgccaca attgccgccg tgaggggcgc cttcgaggac   1860

agatcctacc ccgccgtgtt ctacctgctg caggccgcca tccatggcaa cgagcacgtg   1920

ttctgcgccc tggccagact ggtgacccag tgcatcacca gctactggaa caacaccaga   1980

tgcgccgcct tcgtgaacga ctacagcctg gtgtcctaca tcgtgaccta cctgggcggc   2040

gacctgcctg aggaatgcat ggccgtgtac cgggacctgg tggcccatgt ggaggctctg   2100

gcccagctgg tcgacgactt caccctgcct ggccctgagc tgggaggaca ggcccaggcc   2160

gaactgaacc acctgatgcg ggaccctgct ctgctgcctc ccctggtctg ggattgcgac   2220

ggcctgatga gacacgccgc cctggacagg caccgggact gcagaatcga tgccggcgga   2280

cacgagcctg tgtacgctgc cgcctgcaat gtggccaccg ccgacttcaa ccggaacgac   2340

ggcaggctgc tgcacaacac ccaggccaga gccgccgatg ccgccgacga cagacctcac   2400

agacccgccg actggaccgt gcaccacaag atctactact acgtgctggt gcccgccttc   2460

agcagaggca ggtgctgtac agccggcgtg cggttcgaca gagtgtacgc caccctgcag   2520

aacatggtgg tgcccgagat tgcccctggc gaggaatgcc ccagcgaccc cgtgacagat   2580

cctgcccacc ctctgcaccc tgccaacctg gtggctaaca ccgtgaagcg gatgttccac   2640

aacggcaggg tggtggtgga tggccctgcc atgctgaccc tgcaggtgct ggcccacaac   2700

atggccgaga ggaccacagc cctgctgtgt tctgccgccc ctgacgctgg cgccaatacc   2760

gccagcaccg ccaacatgcg gatcttcgac ggcgccctgc atgctggcgt cctgctgatg   2820

gcccccccagc acctggatca caccatccag aacggcgagt acttttacgt gctgcccgtg   2880

cacgccctgt ttgccggcgc tgaccacgtg gccaacgccc ccaatttccc ccctgccctg   2940

agggatctgg ccagggacgt gcctctggtg cctcctgccc tgggcgccaa ctacttcagc   3000
```

```
agcatccggc agcctgtggt gcagcatgcc agagaatctg ccgctggcga gaacgccctg   3060

acctacgccc tgatggccgg ctacttcaag atgagccccg tggccctgta tcaccagctg   3120

aaaaccggcc tgcaccctgg cttcggcttt accgtggtgc ggcaggacag attcgtgacc   3180

gagaacgtgc tgttcagcga gagagccagc gaggcctact tcctgggcca gctccaggtg   3240

gccagacacg aaacaggcgg gggagtgaat ttcaccctga cccagcccag aggcaacgtg   3300

gatctgggcg tgggctatac agccgtggcc gccaccggca ccgtgagaaa ccccgtgacc   3360

gacatgggca acctgcccca gaacttctac ctgggcaggg gagcccctcc cctgctggat   3420

aatgccgccg ctgtgtacct gaggaacgcc gtggtggccg gcaatagact cggacccgcc   3480

cagcctctgc ctgtgttcgg ctgcgcccag gtgccaagac gggccggaat ggaccacgga   3540

caggacgccg tgtgcgagtt catcgccacc cccgtggcca ccgacatcaa ctactttcgg   3600

aggccctgca accctagagg aagggccgct ggcggagtgt atgccggcga caaggaaggc   3660

gacgtcatcg ccctgatgta cgaccacggc cagagcgatc ccgccagacc ttttgccgcc   3720

accgccaacc cttgggccag ccagaggttc agctacggcg atctgctgta caatggcgcc   3780

taccacctca atggcgccag ccctgtgctg tccccctgct tcaagttctt cacagccgcc   3840

gacatcaccg ccaagcaccg gtgcctggaa aggctgatcg tggagaccgg cagcgccgtg   3900

tctacagcca ccgccgccag cgacgtgcag ttcaagaggc ccccaggctg cagagaactg   3960

gtggaggacc cttgcggcct gttccaggaa gcctacccca tcacctgcgc ctctgatcct   4020

gccctgctgc ggagcgctag agatggcgag gcccacgcca gggaaaccca cttcacccag   4080

tacctgatct acgacgccag ccccctgaag ggcctgagcc tgtga                   4125
```

<210> SEQ ID NO 13
<211> LENGTH: 1686
<212> TYPE: DNA
<213> ORGANISM: Herpes Simplex Virus

<400> SEQUENCE: 13

```
atggagactt cagtcagagg gcacgcagta cggaggcgac gcgccagcac cagatcgcac     60

gccccctcgg cacatagggc ggactccccg gtggaggacg aacccgaagg agggggagtg    120

ggactcatgg aaaccgggta tctccgggca gtctttaacg tggatgatga cagcgaggta    180

gaggcagcgg gtgaaatgga gacagcctcc gaagagccac cccctagacg gcggagagaa    240

gcgagaggac atcccggttc cagacgggca tcagaagcga gggccgcagc tccgcctcga    300

agggcgtcct tccctagacc acgctcagtg acggcgaggt cgcagtccgt ccgcggcaga    360

cgggactcgg ccatcactcg agcgccgagg ggtgggtatc tgggaccgat ggagacagat    420

ccgcgggacg tgctggggcg agtcggaggc agccgggtgg tgccctcgcc cttgttcctc    480

gatgagctta actacgagga ggatgactac cctgctgccg tcgcgcatga cgacggaccc    540

ggagcgaggc cgtccgcgac ggtcgagatt cttgcgggtc gcgtgagcgg accagaattg    600

caggcggcct tccctctcga tcgcttgacg cccagggtag ccgcttggga tgaatccgta    660

cgctcagcac tggcgctggg gcacccagcc ggcttctacc catgcccgga ctccgccttt    720

gggttgtcgc gcgtaggggt catggagaca cactttgcat cgcctgctga tccgaaagtg    780

ttctttcgac aaacactgca gcagggggag gctctggcat ggtatgtcac tggggatgcg    840

atcttggacc tcaccgatcg acgggccaaa acatcgccta gccgggctat ggagacagga    900

ttcctcctcg acgcggctgt acgggtcgcg atcaacggtt gggtatgtgg aacgagattg    960

cataccgaag gacgcggatc ggaacttgac gatcgcgcag cagaacttcg gagacagttc   1020
```

-continued

```
gcatcgctca cggccctccg gccagtggga gcagccgcgg tgccattgct ctccgcggga   1080

ggggctgcgc ctccccaccc gggtccggat gcggccgtgt tccgctcatc gttggggtca   1140

ttgctttact ggcctggcgt ccgggctctg cttggcaggg actgcagggt cgccgccaga   1200

tacgcgggta ggatggaaac gacctatatc gcgacggggg cactgctcgc caggttcaat   1260

cccggtgccg tgaagtgtgt cctgccgcga gaagccgcgt tcgctgggag agtgctggac   1320

gtcctggcgg tgctggcaga gcaaacagta cagtggctct cggtggtagt cggtgcccgc   1380

ttgcatcccc actcagcgca cccggcattt gccgacgtcg aacaggaggc gctgtttcgc   1440

gcccttcccc ttgggtcacc cggagtggtc gcagctgagc acgaagccct tggggataca   1500

gcggcacgcc ggttgctggc gacatcgggt cttaatgcgg tgttgggtgc ggcggtgtac   1560

gcgctccata ccgcgctggc caccgtcact ttgaaatacg cactggcgtg cggggatgca   1620

cgccgacgca gggatgacgc ggcagccgcc agagctgtac ttgcgaccgg attgattctt   1680

cagtag                                                              1686
```